(12) United States Patent
Yang

(10) Patent No.: US 9,801,953 B2
(45) Date of Patent: Oct. 31, 2017

(54) NANOPARTICLES CARRYING NUCLEIC ACID CASSETTES FOR EXPRESSING RNA

(71) Applicant: EMORY UNIVERSITY, Atlanta, GA (US)

(72) Inventor: Lily Yang, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/052,947

(22) Filed: Oct. 14, 2013

(65) Prior Publication Data

US 2014/0105828 A1 Apr. 17, 2014

Related U.S. Application Data

(60) Provisional application No. 61/713,727, filed on Oct. 15, 2012.

(51) Int. Cl.

| A61B 5/055 | (2006.01) |
|---|---|
| A61K 49/00 | (2006.01) |
| A61K 47/48 | (2006.01) |
| A61K 45/06 | (2006.01) |
| A61K 49/18 | (2006.01) |

(52) U.S. Cl.
CPC ........ *A61K 47/48892* (2013.01); *A61K 45/06* (2013.01); *A61K 47/48884* (2013.01); *A61K 49/0067* (2013.01); *A61K 49/1866* (2013.01)

(58) Field of Classification Search
CPC .. A61K 49/1866; A61K 45/06; A61K 49/006; A61K 49/0067; A61K 47/48892; A61K 47/48884
USPC ...................................... 424/9.323
See application file for complete search history.

(56) References Cited

U.S. PATENT DOCUMENTS

| 8,258,288 B2 | 9/2012 | McSwiggen | |
|---|---|---|---|
| 8,313,772 B2 | 11/2012 | Rozema | |
| 2004/0204377 A1 | 10/2004 | Rana | |
| 2005/0008617 A1 | 1/2005 | Chen | |
| 2008/0153771 A1 | 6/2008 | Liu | |
| 2009/0322327 A1* | 12/2009 | Gao | 324/307 |
| 2010/0284921 A1 | 11/2010 | Gordon | |
| 2012/0225017 A1 | 9/2012 | Gombotz | |
| 2012/0225125 A1 | 9/2012 | Unger | |
| 2013/0189367 A1* | 7/2013 | Zhang et al. | 424/493 |

FOREIGN PATENT DOCUMENTS

| EP | 2207903 | 6/2010 |
|---|---|---|
| EP | 2257280 | 12/2010 |
| EP | 2295045 | 3/2011 |
| EP | 2136788 | 10/2011 |
| EP | 1818417 | 2/2014 |
| WO | 2004029213 | 9/2004 |
| WO | 2007016507 | 2/2007 |
| WO | 2007118065 | 10/2007 |
| WO | 2008073856 | 6/2008 |
| WO | 2009114476 | 9/2009 |
| WO | 2009120702 | 10/2009 |
| WO | 2009147246 | 12/2009 |
| WO | 2010048623 | 11/2010 |
| WO | 2012167028 | 12/2012 |

OTHER PUBLICATIONS

Yuan et al., 2010, Oral Oncology 46:698-704.*
Yang et al 2009, Clin. Cancer Res. 15:4722-4732.*
Liu et al., Jun. 2012, J. Cell. Mol. Med. 16:1298-1309.*
Plank et al 2011 Advanced Drug Delivery 63:1300-1331.*
Guo et al., 2011, Biomaterials 32:4283-4292.*
Derfus et al., (2007, Bioconjugate Chem. 18:1391-1396.*
Huynh et al., (2006 BBRC 350:854-859.*
Yang et al., 2008, J. Biomedical Nanotechnol. 4:439-449.*
Ashtari et al 2005, Talanta 67:548-534.*
Barros & Gollob, Safety profile of RNAi nanomedicines, Advanced Drug Delivery Reviews, 2012, 64,1730-1737.
Cho et al., Targeted Delivery of siRNA-Generating DNA Nanocassettes Using Multifunctional Nanoparticles, Small 2013, 9, No. 11, 1964-1973.
Liu et al., A new oncolytic adenoviral vector carrying dual tumour suppressor genes shows potent anti-tumour effect, J. Cell. Mol. Med. vol. 16, No. 6, 2012 pp. 1298-1309.
Medarova et al., In vivo imaging of siRNA delivery and silencing in tumors, Nature Medicine, 2007, vol. 13 No. 3 pp. 372-377.
Medarova et al., Development and Application of a Dual-Purpose Nanoparticle Platform for Delivery and Imaging of siRNA in Tumors, Methods Mol Biol. 2009 ; 555: 1-13.
Plank et al., Magnetically enhanced nucleic acid delivery. Ten years of magnetofection—Progress and prospects, Advanced Drug Delivery Reviews 63 (2011) 1300-1331.
Semple et al., Rational design of cationic lipids for siRNA delivery, Nature Biotechnology, 2010, vol. 28 No. 2 pp. 172-177.
Sliva & Schnierle, Selective gene silencing by viral delivery of short hairpin RNA, Virology Journal 2010, 7:248.
Yuan et al., Dendrimer-triglycine-EGF nanoparticles for tumor imaging and targeted nucleic acid and drug delivery, Oral Oncol, 2010, 46(9): 698-704.
Zuckerman et al. (2010) siRNA knockdown of ribonucleotide reductase inhibits melanoma cell line proliferation alone or synergistically with temozolomide. J Invest Dermatol 131:453-60.
Chen et al., Nanoparticles modified with tumor-targeting scFv deliver siRNA and miRNA for cancer therapy, Mol Ther. 2010,18(9):1650-6.

(Continued)

*Primary Examiner* — Christopher M Babic
*Assistant Examiner* — Kelaginamane T Hiriyanna
(74) *Attorney, Agent, or Firm* — Emory Patent Group

(57) ABSTRACT

This disclosure relates to nanoparticles carrying nucleic acid cassettes for expressing RNA. In certain embodiments, the disclosure relates to improved methods for targeted delivery and expression of siRNAs in vivo using DNA-based siRNA-expressing nanocassettes and receptor-targeted nanoparticles. In certain embodiments, the disclosure relates to methods of targeted delivery of survivin siRNA expressing nanocassettes which enhance sensitivity of human cancer cells to anticancer agents.

4 Claims, 14 Drawing Sheets
(14 of 14 Drawing Sheet(s) Filed in Color)

(56) References Cited

OTHER PUBLICATIONS

Yang et al., Single chain epidermal growth factor receptor antibody conjugated nanoparticles for in vivo tumor targeting and imaging, Small. Feb. 2009;5(2):235-43.
Yang et al. Development of Receptor Targeted Magnetic Iron Oxide Nanoparticles for Efficient Drug Delivery and Tumor Imaging, Journal of Biomedical Nanotechnology, vol. 4, 1-11, 2008.
Yang et al. Receptor-Targeted Nanoparticles for In vivo Imaging of Breast Cancer, Clin Cancer Res 2009;15(14), 4722.

* cited by examiner

1. DNA 1kb ladder
2. Luc siRNA expressing DNA nanocassettes
3. QDs
4. QD-Luc siRNA expressing DNA nanocassettes
5. hATF-QDs
6. hATF-QD siRNA expressing DNA nanocassettes

SEQUENCE LISTING

```
<160> NUMBER OF SEQ ID NOS: 11

<210> SEQ ID NO 1
<211> LENGTH: 69
<212> TYPE: DNA
<213> ORGANISM: Artificial Sequence
<220> FEATURE:
<223> OTHER INFORMATION: Synthetic constructs
<220> FEATURE:
<221> NAME/KEY: misc_feature
<222> LOCATION: (7)..(25)
<223> OTHER INFORMATION: Where n is about 19-23 nucleotides
<220> FEATURE:
<221> NAME/KEY: misc_feature
<222> LOCATION: (34)..(54)
<223> OTHER INFORMATION: Where y is about 19-20 nucleotides

<400> SEQUENCE: 1
```

```
ggatccnnnn nnnnnnnnnn nnnnnttcaa gagayyyyyy yyyyyyyyyy yyytttttg       60 gaaaaagct                                                              69

<210> SEQ ID NO 2
<211> LENGTH: 20
<212> TYPE: DNA
<213> ORGANISM: Artificial Sequence
<220> FEATURE:
<223> OTHER INFORMATION: Synthetic Constructs

<400> SEQUENCE: 2
aagaggcttg caacagtgca                                                  20

<210> SEQ ID NO 3
<211> LENGTH: 23
<212> TYPE: DNA
<213> ORGANISM: Artificial Sequence
<220> FEATURE:
<223> OTHER INFORMATION: Synthetic constructs

<400> SEQUENCE: 3
gaggctggct tcatccactg ccc                                              23

<210> SEQ ID NO 4
<211> LENGTH: 19
<212> TYPE: DNA
<213> ORGANISM: Artificial Sequence
<220> FEATURE:
<223> OTHER INFORMATION: Synthetic constructs

<400> SEQUENCE: 4
cggattacca gggatttca                                                   19

<210> SEQ ID NO 5
<211> LENGTH: 19
<212> TYPE: PRT
<213> ORGANISM: Artificial Sequence
<220> FEATURE:
<223> OTHER INFORMATION: Synthetic constructs

<400> SEQUENCE: 5

Cys Ala Ala Gly Cys Thr Gly Ala Cys Cys Cys Thr Gly Ala Ala Gly
1               5                   10                  15

Thr Thr Cys

<210> SEQ ID NO 6
<211> LENGTH: 20
<212> TYPE: DNA
<213> ORGANISM: Artificial Sequence
<220> FEATURE:
<223> OTHER INFORMATION: Synthetic constructs

<400> SEQUENCE: 6
gatgtgctgc aaggcgatta                                                  20

<210> SEQ ID NO 7
<211> LENGTH: 18
<212> TYPE: DNA
<213> ORGANISM: Artificial Sequence
<220> FEATURE:
<223> OTHER INFORMATION: Synthetic constructs

<400> SEQUENCE: 7
agtgagcgca acgcaatt                                                    18
```

```
<210> SEQ ID NO 8
<211> LENGTH: 18
<212> TYPE: DNA
<213> ORGANISM: Artificial Sequence
<220> FEATURE:
<223> OTHER INFORMATION: Synthetic constructs

<400> SEQUENCE: 8
aactgttggg aagggcga                                                  18

<210> SEQ ID NO 9
<211> LENGTH: 18
<212> TYPE: DNA
<213> ORGANISM: Artificial Sequence
<220> FEATURE:
<223> OTHER INFORMATION: Synthetic constructs

<400> SEQUENCE: 9
agtgagcgca acgcaatt                                                  18

<210> SEQ ID NO 10
<211> LENGTH: 12
<212> TYPE: PRT
<213> ORGANISM: Homo sapiens

<400> SEQUENCE: 10

Cys Gly Gly Gly Pro Lys Lys Lys Arg Lys Val Glu
1               5                   10

<210> SEQ ID NO 11
<211> LENGTH: 20
<212> TYPE: DNA
<213> ORGANISM: Artificial Sequence
<220> FEATURE:
<223> OTHER INFORMATION: Synthetic constructs

<400> SEQUENCE: 11
cagtggatta ccacagctga                                                20
```

US 9,801,953 B2

NANOPARTICLES CARRYING NUCLEIC ACID CASSETTES FOR EXPRESSING RNA

CROSS REFERENCE TO RELATED APPLICATION

This application claims priority to U.S. Provisional Application No. 61/713,727 filed Oct. 15, 2012, hereby incorporated by reference in its entirety.

GOVERNMENT ACKNOWLEDGMENT

This invention was made with government support under Grants R01CA133722, U01CA151810 and U54 CA119338 awarded by the National Institutes of Health. The government has certain rights in the invention.

BACKGROUND

The most aggressive and life threatening forms of cancer frequently develop a resistance to chemotherapy because of high expression of survival genes in these tissues. For example, pancreatic cancer has a very low survival rate and a very high rate of chemotherapy resistance. Moreover, many current chemotherapy treatments are extremely toxic to the patient since they are not targeted to a particular tumor tissue. Taken together, there is a large need to develop alternative and specialized cancer treatments to reduce side effects and tumor resistance to chemotherapy treatments.

RNA interference (RNAi) enables sequence specific gene silencing by promoting degradation of specific mRNAs with short double-stranded RNA molecules (siRNA). Administering naked RNA molecules is not a practical therapeutic strategy because of instability of the siRNA in circulating blood. Unprotected siRNAs are degraded by ribonucleases in serum soon after intravenous delivery.

Formulating siRNA within polymeric or lipid nanoparticles (LNPs) is a strategy to prevent degradation. Stable nucleic acid lipid particle (SNALP) typically contain an ionizable lipid, a neutral helper lipid, cholesterol, and a diffusible polyethylene glycol (PEG)-lipid. See Semple et al., Nature Biotech, 2010, 28(2), 172-6. In another example, transferrin receptor targeted cyclodextrin polymer nanoparticles carrying siRNAs have been reported. See Zuckerman et al., J Invest Dermatol, 2011, 131, 453-60.

Medarova et al. report in vivo imaging of siRNA delivery and silencing in tumors using magnetic iron oxide nanoparticles (IONPs) conjugated with siRNAs. Nat Med, 2007, 13, 372-377.

Chen et al. report nanoparticles modified with tumor-targeting scFv deliver siRNA and microRNA for cancer therapy. See Mol Ther, 2010, 18(9):1650-6.

Sliva and Schnierle report selective gene silencing by viral delivery of short hairpin RNA. See Virology J, 2010, 7:248

Particles and RNA interference are reported in a number of patent references. See, e.g., U.S. Pat. No. 8,313,772, U.S. Pat. No. 8,258,288, U.S. Pat. No. 8,222,220, US201202250, US20120225125, US201002849, US20100284921, US2010048623, US20040204377, US20050008617, EP1818417, EP 2136788, EP 2257280, EP 2295045, EP 2207903, WO2009114476, WO20080153771, WO2004029213, WO2008073856, WO2012167028, WO2007118065.

References cited herein are not an admission of prior art.

SUMMARY

This disclosure relates to nanoparticles carrying nucleic acid cassettes for expressing RNA. In certain embodiments, the disclosure relates to improved methods for targeted delivery and expression of siRNAs in vivo using DNA-based siRNA-expressing nanocassettes and receptor-targeted nanoparticles. In certain embodiments, the disclosure relates to methods of targeted delivery of survivin siRNA expressing nanocassettes which enhance sensitivity of human cancer cells to anticancer agents.

In certain embodiments, the disclosure relates to particles comprising a core with polymer coating wherein the polymer coating is conjugated to a nucleic acid that encodes RNA capable of RNA interference in operable combination with a promoter and wherein a cell targeting molecule is conjugated to the polymer coating. In certain embodiments, the nucleic acid is double stranded DNA having between about 350 and 1500 base pairs or 400 and 1000 base pairs, or 550 and 750 base pairs. In certain embodiments, the polymer coating contains monomers with hydrophobic and hydrophilic groups. In certain embodiments, the hydrophilic groups are amine and carboxylic acid groups. In certain embodiments, the nucleic acid is double stranded DNA. In certain embodiments, the RNA capable of RNA interference is RNA that forms a hairpin. In certain embodiments, the RNA capable of RNA interference is a short hairpin RNA. In certain embodiments, the RNA capable of RNA interference comprises a survivin sequence of greater than 15, 16, 17, or 18 nucleotides. In certain embodiments, the promoter is U6 or H1.

In certain embodiments, the polymer coating is conjugated to a nucleic acid that encodes microRNA.

In certain embodiments, the core of the particle has a size of about between 5 nm and 100 nm, or 20 nm and 200 nm, or 5 nm and 500 nm in diameter. In certain embodiments, the core is a metal, combination of metals, a semiconductor, quantum dot, gold, silver, iron, or an iron oxide particle.

In certain embodiments, the cell targeting molecule is a polypeptide, ligand, receptor, protein, antibody, or antibody fragment. In certain embodiments, the cell targeting molecule is a ligand that targets a receptor specifically expressed on tumor cells. In certain embodiments, the cell targeting molecule is human ATF (hATF) peptide or fragment thereof. In certain embodiments, the cell targeting molecule is a tumor-targeting human monoclonal antibody or comprises a single-chain variable fragment (scFv) thereof.

In certain embodiments, particles disclosed herein further comprising an anticancer agent.

In certain embodiments, the anticancer agent is conjugated to the polymer coating through carboxylic acid groups. In certain embodiments, the anticancer agent is trapped inside the polymer coating in the area of the hydrophobic groups.

In certain embodiments, the disclosure relates to methods of treating a disease or condition associated with an overexpression of a gene comprising administering particles disclosed herein with a polymer coating wherein the polymer is conjugated to a nucleic acid that encodes a RNA capable of RNA interference of the overexpressed gene in operable combination with a promoter and wherein the polymer is conjugated to a cell targeting molecule to a subject in need thereof in an effective amount.

In certain embodiments, the disease or condition is cancer and the subject is diagnosed with cancer. In certain embodiments, the cancer is breast or pancreatic cancer. In certain embodiments, the particles are administered in combination with another anticancer agent.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DISCUSSION

Figure 1A:
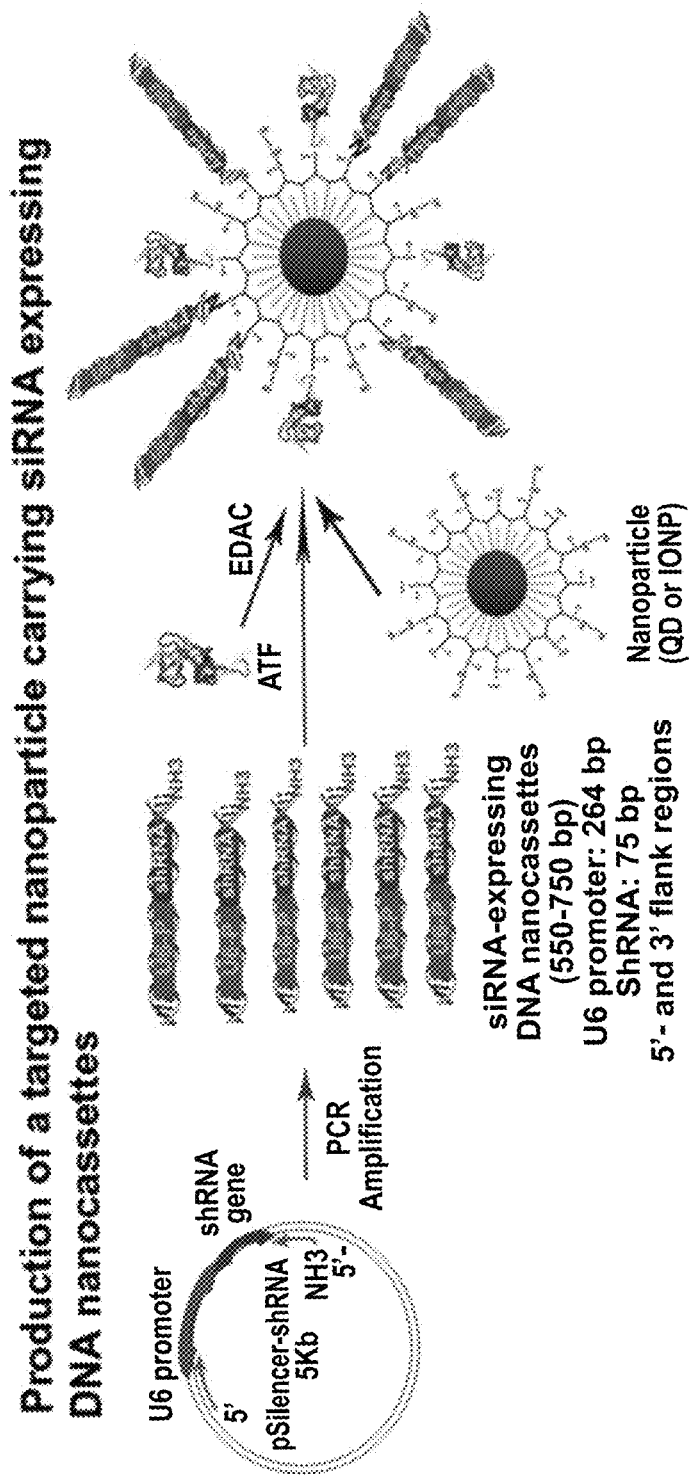
FIG. 1 schematically illustrates siRNA-nanogenerators and a proposed mechanism of targeted delivery and production of siRNAs in cells A) Production of uPAR-targeted nanoparticles for delivery of siRNA-expressing DNA nanocassettes. B) Proposed mechanism of internalization of the nanoparticles and expression of siRNAs from the nanocassettes.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, the term "combination with" when used to describe administration with an additional treatment means that the agent may be administered prior to, together with, or after the additional treatment, or a combination thereof.

As used herein, "subject" refers to any animal, typically a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" can be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample particle compared to a control without the particle. It can also be identified by a change in relevant biomarker or gene expression profile, such as PSA for prostate cancer, HER2 for breast cancer, or others.

The terms "nucleic acid sequence" refer to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The terms "a nucleic acid sequence encoding" a specified polypeptide refer to a nucleic acid sequence comprising the coding region of a gene or in other words the nucleic acid sequence which encodes a product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc., may be placed in close proximity to the coding region if needed to permit proper initiation of transcription and/or correct processing of the primary RNA transcript. Alternatively, the coding region utilized in the expression vectors may contain endogenous enhancers, exogenous promoters, splice junctions, intervening sequences, polyadenylation signals, etc., or a combination of both endogenous and exogenous control elements.

As used herein, the term "exogenous promoter" refers to a promoter in operable combination with a coding region wherein the promoter is not the promoter naturally associated with the coding region in the genome of an organism. The promoter which is naturally associated or linked to a coding region in the genome is referred to as the "endogenous promoter" for that coding region.

The term "expression" when used in reference to a nucleic acid sequence refers to the process of converting genetic information encoded in a gene into RNA (e.g., mRNA, rRNA, tRNA, shRNA, or miRNA) through "transcription" of the gene (i.e., via the enzymatic action of an RNA polymerase), and into protein where applicable (as when a gene encodes a protein), through "translation" of mRNA.

The terms "in operable combination," "in operable order," and "operably linked" refer to the linkage of nucleic acid sequences in such a manner that a nucleic acid molecule capable of directing the transcription of a given gene and/or the synthesis of a desired RNA or protein molecule is produced.

Transcriptional control signals in eukaryotes comprise "promoter" and "enhancer" elements. Promoters and enhancers consist of short arrays of DNA sequences that interact specifically with cellular proteins involved in transcription (see, for e.g., Maniatis, et al. (1987) Science 236:1237; herein incorporated by reference). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Maniatis, et al. (1987), supra; herein incorporated by reference).

The terms "promoter" or "promoter sequence" refer to a DNA sequence that is located at the 5' end (i.e., precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of RNA from the gene. The promoter, therefore, serves as a transcriptional regulatory element and also provides a site for initiation of transcription of the gene into RNA.

The term "promoter region" refers to the region immediately upstream of the coding region of a DNA polymer, and is typically between about 500 bp and 4 kb in length. Promoters may be tissue specific or cell specific. The term "cell type specific" as applied to a promoter refers to a promoter that is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody that is specific for the polypeptide product encoded by the nucleotide sequence of interest whose expression is controlled by the promoter. A labeled (e.g., peroxidase conjugated) secondary antibody that is specific for the primary antibody is allowed to bind to the sectioned tissue and specific binding detected (e.g. with avidin/biotin) by microscopy.

RNA Interference

RNA interference initially discovered in plants as Post-Transcriptional Gene Silencing (PTGS), is a highly conserved mechanism triggered by double-stranded RNA (dsRNA) and able to down regulate transcript of genes homologous to the dsRNA. The dsRNA is first processed by Dicer into short duplexes of 21-23 nt, called short interfering RNAs (siRNAs). Incorporated in RNA-induced silencing complex (RISC), they are able to mediate gene silencing through cleavage of the target mRNA.

"siRNA" or "small-interfering ribonucleic acid" refers to two strands of ribonucleotides which hybridize along a complementary region under physiological conditions. The siRNA molecules comprise a double-stranded region which is substantially identical to a region of the mRNA of the target gene. A region with 100% identity to the corresponding sequence of the target gene is suitable. This state is referred to as "fully complementary". However, the region may also contain one, two or three mismatches as compared to the corresponding region of the target gene, depending on the length of the region of the mRNA that is targeted, and as such may be not fully complementary. Methods to analyze and identify siRNAs with sufficient sequence identity in order to effectively inhibit expression of a specific target sequence are known in the art. A suitable mRNA target region would be the coding region. Also suitable are untranslated regions, such as the 5'-UTR, the 3'-UTR, and splice junctions as long as the regions are unique to the mRNA target and not directed to a mRNA poly A tail.

The length of the region of the siRNA complementary to the target, in accordance with the present disclosure, may be from 15 to 100 nucleotides, 18 to 25 nucleotides, 20 to 23 nucleotides, or more than 15, 16, 17 or 18 nucleotides. Where there are mismatches to the corresponding target region, the length of the complementary region is generally required to be somewhat longer. In certain embodiments, the RNA capable of RNA interference comprises a human survivin sequence of 18 to 25 nucleotides or greater than 15, 16, 17, or 18 nucleotides. Human survivin mRNA sequence (also known as *homo sapiens* baculoviral IAP repeat containing 5 (BIRC5) transcript variant 1) is ACCESSION NM_001168.2, available at http://www.ncbi.nlm.nih.gov/gene/332, hereby incorporated by reference. Alternatively spliced transcript variants encoding distinct isoforms have been found for this gene. This gene is a member of the inhibitor of apoptosis (IAP) gene family, which encode negative regulatory proteins that prevent apoptotic cell death.

In certain embodiments, the RNA capable of RNA interference comprises an mRNA sequence of human baculoviral inhibition of apoptosis protein repeat (BIR) domain found in inhibitors of apoptosis proteins (IAPB) and other proteins. In higher eukaryotes, BIR domains inhibit apoptosis by acting as direct inhibitors of the caspase family of protease enzymes.

Nanoparticles for Targeted Delivery of siRNA-Generating DNA Nanocassettes

In certain embodiments, the disclosure relates to multifunctional nanoparticles comprising three interchangeable components—a targeting ligand, the nanoparticle, and the cargo. The targeting ligand can consist of a ligand that targets a receptor specifically expressed on tumor cells (such as the amino terminal fragment of urokinase plasminogen activator). The nanoparticles can be either Quantum Dots (QDs) that can be imaged optically, or iron oxide nanoparticles (IONPs) that can be imaged via MRI. The cargo is either a DNA cassette coding for a siRNA against an oncogene or survival factor, a chemotherapy drug or both. These three components allow direct targeting of nanoparticles for tumor-specific imaging and tumor-specific treatment, and increases sensitivity to chemotherapy drugs by reducing expression of survival genes.

Since siRNA is expressed from a RNA polymerase III (e.g., U6 or H1) promoter, a short hairpin siRNA (shRNA) gene may be cloned into expression vectors containing a polymerase III promoter to produce shRNAs from plasmid or viral vectors following transfecting into cells. See Brummelkamp et al., Science, 2002, 296, 550-553; Miyagishi & Taira, Nat. Biotechnol, 2002, 20, 497-500; McAnuff et al, J. Pharm. Sci. 2007, 96, 2922-2930; Bot et al., Blood, 2005, 106, 1147-1153. The shRNAs are further processed into siRNAs by a cellular endoribonuclease.

Although gene silencing using viral vectors has been reported, potential inflammatory and immunogenic effects may prevent their repeated administration. Additionally, most viral vectors have similar sizes to nanoparticles but can only carry one copy of shRNA gene in each vector and, therefore, have relatively low efficiency for delivering the shRNA gene and generating siRNAs. Limited copies of the plasmids can be encapsulated or conjugated to a single nanoparticle with a size less than 100 nm, which is believed to be optimal size for intratumoral delivery. See Wong et al., Proc. Natl. Acad. Sci. USA 2011, 108, 2426-2431.

DNA cassettes expressing shRNA containing a U6 promoter and a shRNA gene can be synthesized by a two-step PCR amplification protocol. See Castanotto et al., RNA, 2002, 8, 1454-1460 and Gou et al., FEBS Lett., 2003, 548, 113-118.

A multifunctional siRNA delivery nanoparticle platform has been developed that combines the imaging capability of the nanoparticles with receptor-mediated delivery of siRNA-expressing DNA cassettes. In certain embodiments provided herein is an improved theranostic nanoparticle that contains a polymer-coated nanoparticle core, e.g., a fluorescent quantum dot (QD) or MRI contrast enhancing magnetic iron oxide nanoparticle (IONP), conjugated with about 10 to 20 DNA nanocassettes that contain a U6 promoter and a shRNA gene for in vivo siRNA gene expression following intracellular delivery. The nanoparticle is conjugated to the amino terminal fragment (ATF) of the urokinase plasminogen activator (uPA), which targets its cellular receptor, uPAR (FIG. 1A). This receptor is highly expressed in tumors, angiogenic endothelial, and stromal cells in many types of human cancers. See Nielsen et al., Int. J. Cancer 2007, 120, 2086 2095; Blasi & Carmeliet, Nat. Rev. Mol. Cell Biol. 2002, 3, 932-943; Pyke et al., Cancer Res, 1993, 53, 1911-1915.

Figure 1B:
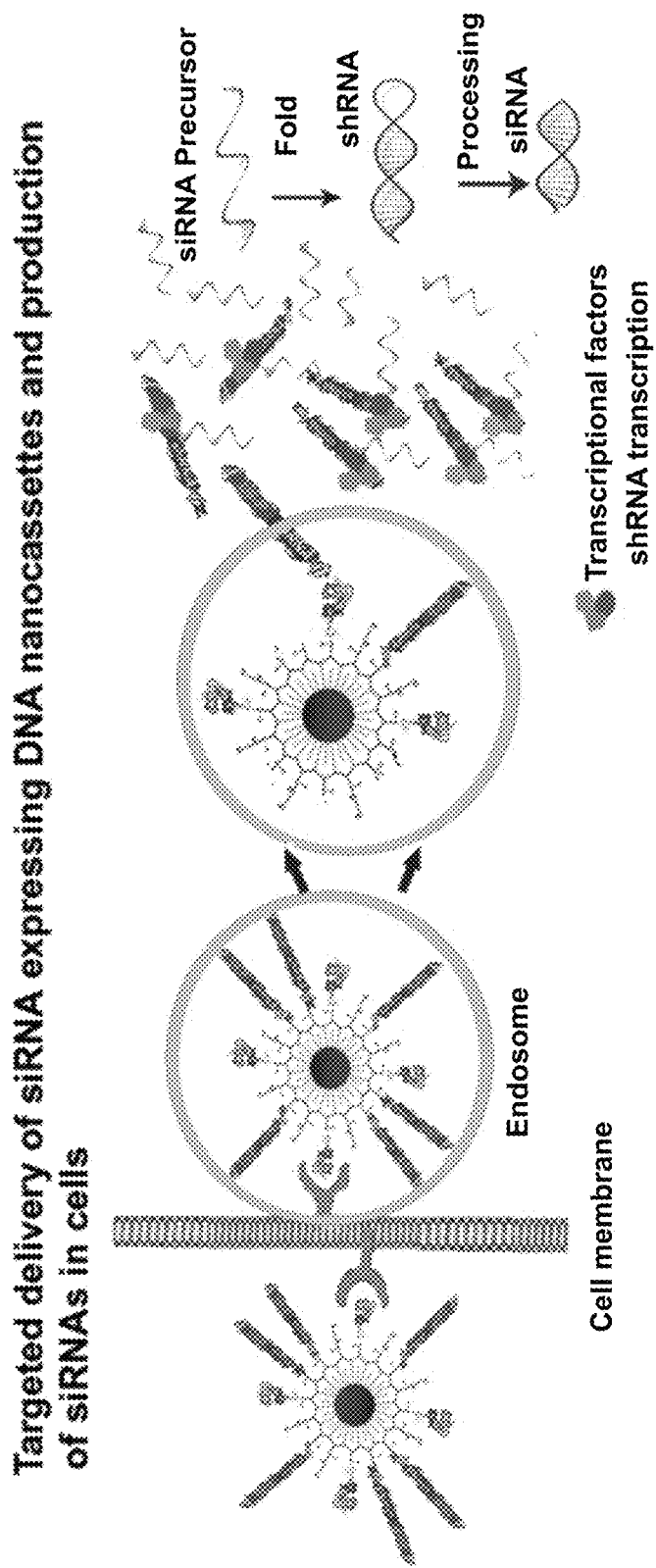

Target specificity of uPAR-targeted nanoparticles in optical and MRI imaging of pancreatic cancers in animal tumor models was reported. See Yang et al., Gastroenterology 2009, 136, 1514-1525 and Yang et al., Clinical Cancer Res., 2009, 15, 4722-4732. Since the binding of ATF conjugated nanoparticles to uPAR leads to the internalization of the nanoparticles, it is believed that endocytosis of the nanoparticle-DNA-nanocassettes into the endosomes results in the cleavage of the amide bond between nanoparticles and DNA cassettes and release of DNA-cassettes into cytoplasm. After DNA cassettes enter into the cell nucleus, interactions of cellular transcriptional factors with the U6 promoter of the DNA-nanocassettes activate transcription of shRNA genes, which are then processed into double-stranded siRNAs for targeted gene silencing (FIG. 1B). These nanoparticles have imaging capability with targeted delivery of siRNA-expressing DNA cassettes. End protected double stranded DNA fragments produced by PCR amplification are nanometer-sized DNA cassettes that have a high stability in the blood and tissues. Nanoparticle conjugated DNA cassettes should have longer half-life in the blood circulation compared with the delivery of unconjugated siRNAs or nanocassettes alone.

To solve the problem of a low delivery efficiency of siRNAs into cells, uPAR-targeted nanoparticles were used to bring the siRNA expressing nanocassettes into tumors as well as inside tumor cells. The uPAR targeted nanoparticles play a role in efficient delivery of siRNA expressing DNA nanocassettes into tumor cells since low levels of QDs were found in the cells and tumors from the mice treated with non-targeted nanoparticles iRNA nanocassettes. In tumor-bearing mice, a marked inhibition of luciferase activity was only detected in the tumors of the mice following systemic delivery of uPAR-targeted nanoparticles carrying Luc siRNA cassettes, but not in the tumors of the mice that received non-targeted nanoparticles-Luc siRNA cassettes. It is believed that an increase in tumor accumulation and receptor-mediated internalization of the nanoparticles into cells contribute to the significant inhibition of luciferase gene expression in the tumor xenografts in nude mice.

Additionally, the ability of delivery of over ten siRNA expressing DNA nanocassettes by a single nanoparticle and expression of multiple copies siRNAs from each DNA cassette further enhanced the efficiency of knocking-down gene expression. The ability and efficiency of the DNA nanocassettes to express a shRNA gene after being delivered into cells was demonstrated. It is possible that the DNA nanocassettes can be released from the nanoparticles by cleaving the amide bond between the nanoparticles and DNA cassettes or by degradation of polymer-coating in the endosomes or lysosomes. These small DNA fragments may pass through the endosomal membrane. Additionally, conjugation of the DNA fragments at the 3'-end of the expressing cassettes makes it possible to express the shRNA gene from the nanoparticle-conjugated nanocassettes after endosomal escape of the nanoparticles.

The advantage of intracellular expression of siRNAs from the DNA cassettes has also been shown in vitro in tumor cells that received an equal molar concentration of the DNA cassettes delivered by the nanoparticles or RNA-based siRNAs. Furthermore, strong and targeted gene silencing effects following delivery of luciferase siRNA expressing nanocassettes using the receptor-targeted nanoparticles have been shown in a human breast cancer xenograft model in nude mice. The combination of targeted delivery and in vivo expression of siRNAs enabled significant inhibition of the level of luciferase gene expression in the tumors for over 6 days. Therefore, targeted delivery of the U6 promoter siRNA expressing DNA nanocassettes using nanoparticles has increased delivery efficiency as well as enhanced the effectiveness and duration of gene silencing in cancer cells.

Drug resistance is the major challenge in cancer treatment. It is believed that cell survival pathways, especially inhibition of proteins in the apoptotic family, such as survivin, confer apoptosis or drug resistance in cancer cells. See Peng et al., J. Biol. Chem, 2006, 281, 25903-25914; Alfieri, Nat. Rev. Cancer 2008, 8, 61-70; Yang et al., Cancer Res. 2003, 63, 6815-6824. Survivin is highly expressed in many human cancer types and can interact with other proteins to block apoptosis.

Survivin siRNA expressing DNA nanocassettes were produced. uPAR-targeted delivery of the nanocassettes inhibited survivin gene expression and led to the activation of apoptotic cell death in human cancer cells. Since cancer cells develop various mechanisms to resist cell death, the combination of activation of the apoptotic pathway by drug treatment with inhibition of anti-apoptotic factors, such as survivin, using siRNAs can produce more potent anti-tumor effects on drug resistant tumor cells.

The combination of a chemotherapy drug, gemcitabine, with survivin siRNA nanocassette delivery significantly enhanced the sensitivity of human pancreatic cancer cells to the drug treatment. It is feasible to produce multifunctional nanoparticles carrying both siRNA expressing nanocassettes and chemotherapy drugs for effective cancer therapy. Magnetic IONPs carrying siRNA expressing nanocassettes may be used as theranostic siRNA nanoparticles for targeted therapy and non-invasive imaging of the therapeutic response in human patients.

The advantages of this DNA-based siRNA generating nanoparticle delivery system include: 1) highly stable and small size DNA fragments containing both the promoter and gene sequences for expressing siRNAs inside cells; 2) the receptor targeted nanoparticle carrier that allows efficient delivery into target tissues as well as intracellular delivery; 3) the nanoparticles are also imaging probes that enable noninvasive imaging of siRNA nanocassette delivery and tumor response to therapy; and 4) the capability of the nanoparticle carrier for simultaneous delivery of therapeutic agents that activate cell death (e.g. anticancer agents) and inhibit cell survival pathways (siRNAs) can enhance the effectiveness of cancer therapy.

Methods of Use

In certain embodiments, it is contemplated that the siRNA delivery approach using nanoparticles disclosed herein can be used to knock-down any genes of interest. For enhancement of the effect of chemotherapy drugs by inhibition of apoptosis resistant pathways, the siRNAs for the following genes can be used: XIAP, HIF-1alpha, survivin, Bcl-2, AKT, K-ras, Her-2, EGFR. Ligands or antibodies or fragments to these gene products may be used for targeting the nanoparticle to cancerous cells.

In certain embodiments, the disclosure relates to targeted nanoparticles disclosed herein containing a chemotherapy drug and siRNA gene expressing cassettes that inhibit the expression of survivin, HIF-1 alpha, and K-ras for use in a combination therapy in breast and pancreatic cancer.

In certain embodiments, particles disclosed herein comprise nucleic acids that encode siRNA targeting mRNA of human cancer associated genes such as those selected from baculoviral IAP repeat containing 3, baculoviral IAP repeat containing 7, tumor protein p53, tumor protein p53 regulated apoptosis inducing protein 1, tumor protein p73, vascular endothelial growth factor A, v-akt murine thymoma viral oncogene, phosphatase and tensin, B-cell CLL/lymphoma 2, signal transducer and activator of transcription 3, epidermal growth factor receptor, v-erb-b2 avian erythroblastic leukemia viral oncogene, tumor necrosis factor, tumor necrosis factor superfamily member 14, nuclear factor of kappa light polypeptide gene enhancer in B-cells 1, catenin (cadherin-associated protein) beta 1, transforming growth factor beta 1, cyclin-dependent kinase inhibitor 1A, caspase 3, caspase 8, caspase 9, telomerase reverse transcriptase, hypoxia inducible factor 1 alpha subunit, ATP-binding cassette subfamily B, cyclin-dependent kinase inhibitor 2A, v-myc avian myelocytomatosis viral oncogene, insulin-like growth factor 1, matrix metallopeptidase 7, matrix metallopeptidase 9, interleukin 8, cyclin B1, cyclin D1, chemokine (C-C motif) ligand 2, cadherin 1, E-cadherin, mitogen-activated protein kinase 1, interferon gamma, tumor necrosis factor (ligand) superfamily member 10, microtubule-associated protein tau, X-linked inhibitor of apoptosis, Fas cell surface death receptor, retinoblastoma 1, BCL2-like 2, BCL2-associated X protein, BCL2-antagonist/killer 1, caveolin 1, caveolae protein, mechanistic target of rapamycin, v-kit Hardy-Zuckerman 4 feline sarcoma viral oncogene, mitogen-activated protein kinase 14, adenomatous polyposis *coli*, aurora kinase B, cyclin-dependent kinase 1, cyclin-dependent kinase 4, cyclin-dependent kinase inhibitor 1B, heme oxygenase (decycling) 1, notch 1, notch 2, secreted phosphoprotein 1, mitogen-activated protein kinase 3, runt-related transcription factor 1, forkhead box O3, forkhead box P3, jun proto-oncogene, poly (ADP-ribose) polymerase 1, Harvey rat sarcoma viral oncogene, glycogen synthase kinase 3 beta, nitric oxide synthase 2, ras-related C3 botulinum toxin substrate 1, E1A binding protein p300, Fas ligand, ATP-binding cassette G2, CREB binding protein, protein kinase C alpha, fms-related tyrosine kinase 3, fibroblast growth factor 2, O-6-methylguanine-DNA methyltransferase, checkpoint kinase 2, diablo IAP-binding mitochondrial protein, parkinson protein 2, polo-like kinase 1, transcription factor 7-like 2, E2F transcription factor 1, high mobility group box 1, promyelocytic leukemia, BCL2-like 1, urokinase plasminogen activator, tumor necrosis factor receptor superfamily member 1A, proliferating cell nuclear antigen, urokinase receptor plasminogen activator, APEX nuclease, lectin galactoside-binding soluble 3, myeloid cell leukemia sequence 1, cannabinoid receptor 1, gap junction protein alpha 1, antigen identified by monoclonal antibody Ki-67, calcium-sensing receptor, thrombospondin 1, POU class 5 homeobox 1, hepatocyte nuclear factor 4 alpha, transforming growth factor beta receptor II, platelet-derived growth factor receptor alpha polypeptide, runt-related transcription factor 2, vascular endothelial growth factor C, early growth response 1, angiopoietin 2, BMI1 polycomb ring finger oncogen, parkinson protein 7, v-myc avian myelocytomatosis viral oncogene neuroblastoma, v-akt murine thymoma viral oncogene homolog 2, H2A histone family member X, tuberous sclerosis 2, exportin 1, peptidylprolyl cis/trans isomerase NIMA-interacting 1, dickkopf WNT signaling pathway inhibitor 1, beclin 1, platelet-derived growth factor beta polypeptide, cortactin, colony stimulating factor 2, fused in sarcoma, ets variant 6, GATA binding protein 1, RAN member RAS oncogene, Kruppel-like factor 4, Kruppel-like factor 5, lymphoid enhancer-binding factor 1, histone deacetylase 6, stathmin 1, folate hydrolase 1, RAS p21 protein activator 1, serine/arginine-rich splicing factor 1, glypican 3, cell adhesion molecule 1, wingless-type MMTV integration site family, member 1, platelet-derived growth factor alpha polypeptide, junction plakoglobin, protein arginine methyltransferase 1, interleukin 11, retinoblastoma-like 2, E2F transcription factor 3, tumor-associated calcium signal transducer 2, XIAP associated factor 1, microtubule-associated protein 4, sirtuin 6, Wilms tumor 1 associated protein, or combinations thereof.

In certain embodiments, the polymer coating is conjugated to a nucleic acid that encodes microRNA. Contemplated microRNA include cancer associated microRNA 34a, microRNA 203, microRNA 16-1, microRNA 218-1, microRNA 494, microRNA 320a, microRNA 542, and microRNA 218-2.

In certain embodiments, it is contemplated that the nanoparticles could be used as a delivery method for many different diseases or conditions by varying the DNA cassette to encode siRNA or microRNA associated with the disease or condition and/or varying targeting molecule for cells associated the disease or condition.

Figure 8:
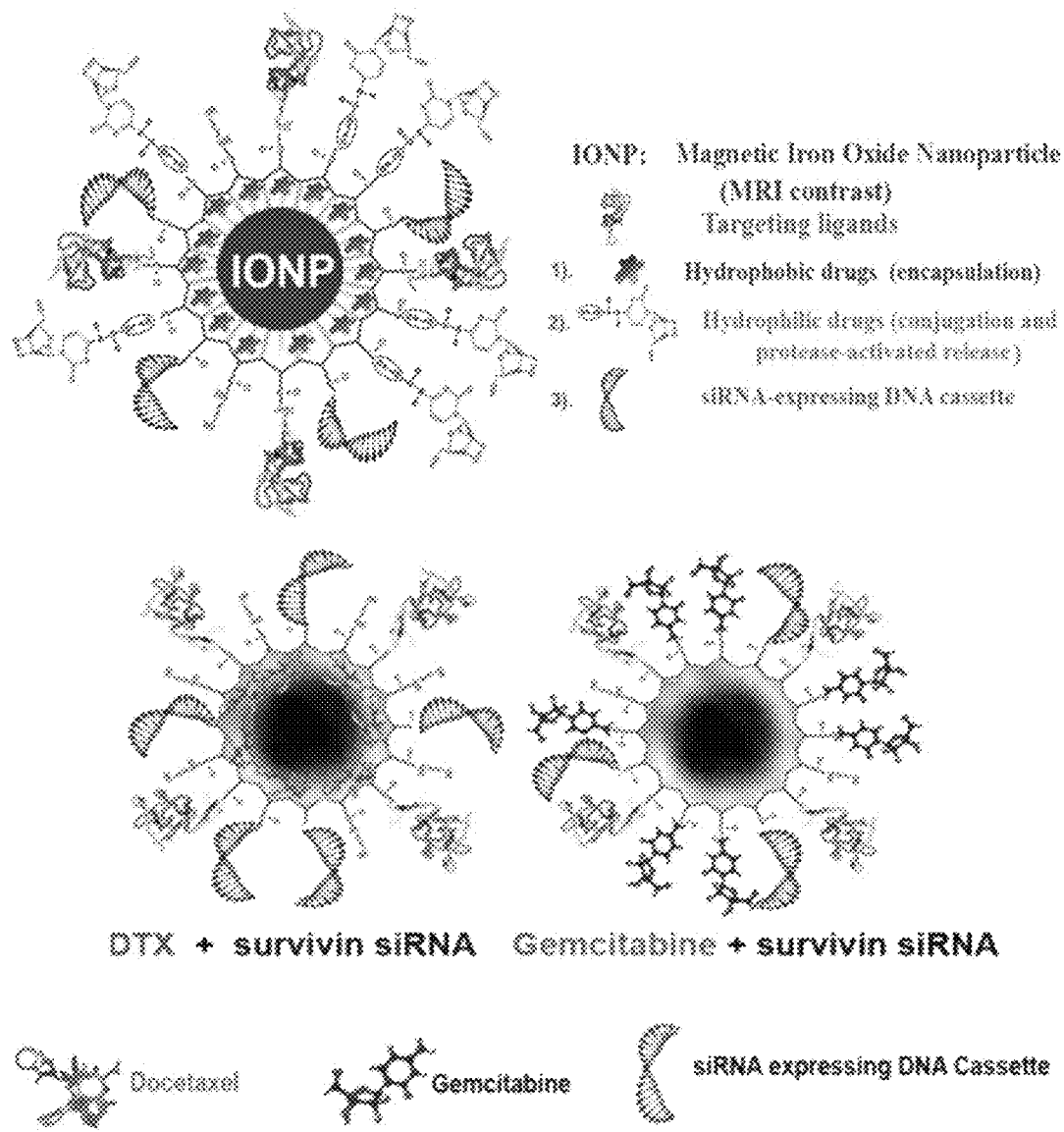
FIG. 8 illustrates certain embodiments of the disclosure. The top illustrates a multifunctional theranostic nanoparticle carrying chemotherapy drugs and siRNA expressing DNA cassettes targeting cell survival genes for the treatment of drug resistant cancer cells. The bottom illustrates two theranostic nanoparticle systems for delivering siRNA expressing DNA-cassettes: right side illustrates targeted delivery of siRNA expressing DNA-cassettes and the left side illustrates targeted and simultaneous delivery of siRNA expressing DNA-cassettes and chemotherapy drugs.

The use of a DNA cassette encoding siRNA is of particular interest compared to other nanoparticle siRNA delivery technologies. A major complication with traditional gene silencing approaches include the lack of specific delivery, inefficient delivery due to unstable siRNAs, and high costs of RNA production. This technology circumvents these challenges by targeting a stable DNA cassette encoding the siRNA specifically to tumors. Once internalized, it is believed that the DNA is cleaved from the nanoparticle in the lysosomes and transported into the nucleus where it can be transcribed into shRNA and initiate the RNAi system of the cell. The siRNA carrying nanoparticles can be used alone or in conjunction with chemotherapy drug containing nanoparticles (See FIG. 8).

In certain embodiments, the disclosure relates to methods of treating a disease or condition associated with an overexpression of a gene comprising administering an effective amount a pharmaceutical composition comprising a particle with a polymer coating wherein the polymer is conjugated to a nucleic acid that encodes a RNA capable of RNA interference of the overexpressed gene in operable combination with a promoter and wherein the polymer is conjugated to a cell targeting molecule to a subject in need thereof.

In certain embodiments, the disclosure relates to methods of treating a disease or condition comprising administering an effective amount a pharmaceutical composition comprising a particle with a polymer coating wherein the polymer is conjugated to a nucleic acid that encodes a microRNA in operable combination with a promoter and wherein the polymer is conjugated to a cell targeting molecule to a subject in need thereof.

The particles of the present disclosure can be administered to a subject either alone or as a part of a pharmaceutical composition.

In certain embodiments, the disease or condition is cancer and the subject is diagnosed with cancer. In certain embodiments, the cancer is breast or pancreatic cancer. In certain embodiments, the disclosure relates to treating or preventing cancer with particles disclosed herein wherein the cancer is selected from brain, lung, cervical, ovarian, colon, breast, gastric, skin, ovarian, pancreatic, prostate, neck, and renal cancer.

Optionally, the particles are administered in combination with a second anticancer agent. The second anticancer agent may be selected from temozolamide, bevacizumab, procarbazine, lomustine, vincristine, gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vinblastine, vindesine, vinorelbine, taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, combretastatin, thalidomide, and/or lenalidomide or combinations thereof.

In certain embodiments, the disclosure contemplates imaging and effecting cell lysis with particles using iron or iron oxide cores. See WO2009/120702.

In certain embodiments, the disclosure relates to targeting of cancer by local hyperthermia using composition and methods disclosed herein. Local hyperthermia can lead to induction of apoptosis, heat-shock protein release, and chemotherapy agent sensitivity of cancer cells by exposure of cancer cells containing particles with an iron or iron oxide core to an alternating magnetic fields (<1000 kHz) that are safe to normal cells.

In certain embodiments, the disclosure relates to methods for lysis of a cancer cells comprising, administering to a subject particles disclosed herein and adjusting magnetic fields proximate the subject to cause cell lysis of cancer cell that absorb the particles after administration. Typically, the magnetic field is an oscillating magnetic field and the particles are heated to at least 37° C. in vivo typically greater than 41° C.

Pharmaceutical Compositions

In certain embodiments, the disclosure relates to pharmaceutical compositions comprising particles disclosed herein and a pharmaceutically acceptable excipient. In certain embodiments, the composition is a pill or in a capsule or the composition is an aqueous buffer, e.g., a pH between 6 and 8. In certain embodiments, the pharmaceutically acceptable excipient is selected from a filler, glidant, binder, disintegrant, lubricant, and saccharide. Optionally, the pharmaceutical composition further comprises a second anticancer agent.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil and viscoleo) and injectable organic esters such as ethyl oleate.

Prevention of the action of microorganisms may be controlled by addition of any of various antibacterial and antifungal agents, example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the particles may be admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar and as high molecular weight polyethylene glycols, and the like.

Solid dosage forms such as tablets, capsules, pills, and granules can be prepared with coatings and shells, such as enteric coatings and others well known in the art. They may contain opacifying agents, and can also be of such composition that they release the particles in a certain part of the intestinal tract in a delayed manner. Examples of embedding compositions which can be used are polymeric substances and waxes.

Liquid dosage forms for oral administration include pharmaceutically acceptable emulsions, solutions, suspensions, syrups, and elixirs. In addition to the particles, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, viscoleo, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents. Suspensions, in addition to the particles, may contain suspending agents, as for example, ethoxylated iso-stearyl alcohols, polyoxyethylene sorbitol and sorbitan esters, microcrystalline cellulose, aluminum metahydroxide, bentonite agar-agar and tragacanth, or mixtures of these substances, and the like.

Pharmaceutical compositions typically comprise an effective amount of particles and a suitable pharmaceutical acceptable carrier. The preparations can be prepared in a manner known per se, which usually involves mixing the particles according to the disclosure with the one or more pharmaceutically acceptable carriers, and, if desired, in combination with other pharmaceutical active compounds, when necessary under aseptic conditions. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

The pharmaceutical preparations of the disclosure are preferably in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain between 1 and 1000 mg, and usually between 5 and 500 mg, of the particles of the disclosure e.g., about 10, 25, 50, 100, 200, 300 or 400 mg per unit dosage.

The particles can be administered by a variety of routes including the oral, ocular, rectal, transdermal, subcutaneous, intravenous, intramuscular or intranasal routes, depending mainly on the specific preparation used. The particles will generally be administered in an "effective amount," by which it is meant any amount of particles that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the subject per day, more often between 0.1 and 500 mg, such as between 1 and 250 mg, for example about 5, 10, 20, 50, 100, 150, 200 or 250 mg, per kilogram body weight of the subject per day, which can be administered as a single daily dose, divided over one or more daily doses. The amount(s) to be administered, the route of administration and the further treatment regimen can be determined by the treating clinician, depending on factors such as the age, gender and general condition of the subject and the nature and severity of the disease/symptoms to be treated.

Formulations containing particles described herein can be prepared using a pharmaceutically acceptable carrier composed of materials that are considered safe and effective and can be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which can include plasticizers, pigments, colorants, stabilizing agents, and glidants. Delayed release, extended release, and/or pulsatile release dosage formulations can be prepared as described in standard references such as "Pharmaceutical dosage form tablets," eds. Liberman et. al. (New York, Marcel Dekker, Inc., 1989), "Remington—The science and practice of pharmacy," 20th ed., Lippincott Williams & Wilkins, Baltimore, Md., 2000, and "Pharmaceutical dosage forms and drug delivery systems," 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard decomposition reactions which include, by way of example, oxidative reactions.

EXAMPLES

Receptor-Targeted Nanoparticles Carrying siRNA-Expressing DNA Nanocassettes

Figure 2A:
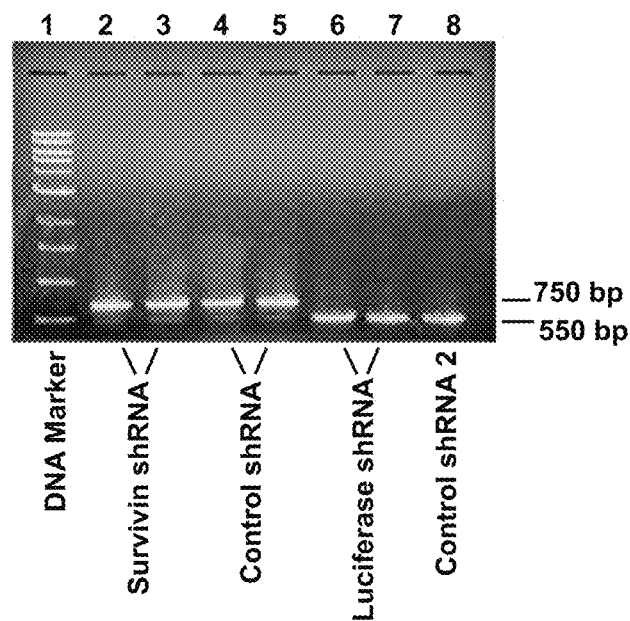
FIG. 2 shows data on the characterization of targeted nanoparticles carrying siRNA expressing DNA nanocassettes. A) Gel electrophoresis analysis of PCR products. The gel picture shows PCR products of Survivin siRNA (750 bp), control siRNA (750 bp), luciferase siRNA (550 bp) and control siRNA (550 bp) expressing DNA cassettes. B) Gel electrophoresis of QD-DNA nanocassettes. Red QD (emission wavelength of 620 nm) and green DNA fluorescent signals were detected on the gel. Left: red QD; Middle: DNA green fluorescence; Right: overlaying QD with DNA-staining image. QDs with DNA nanocassettes showed orange color. C) Nanoparticle size measurements by dynamic light scattering.
Figure 2B:
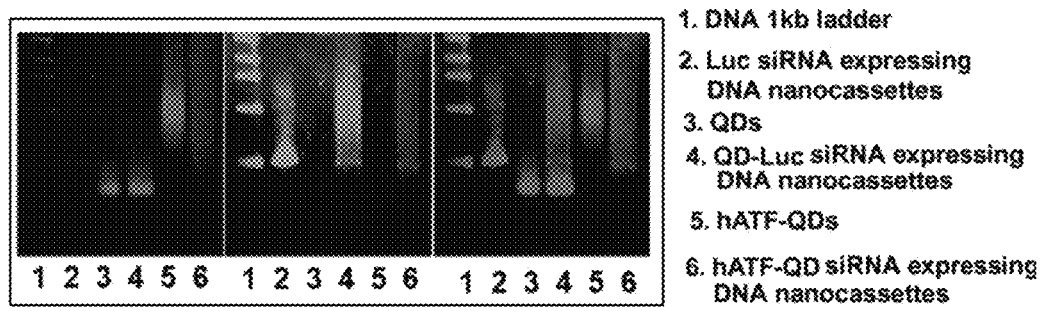
Figure 2C:
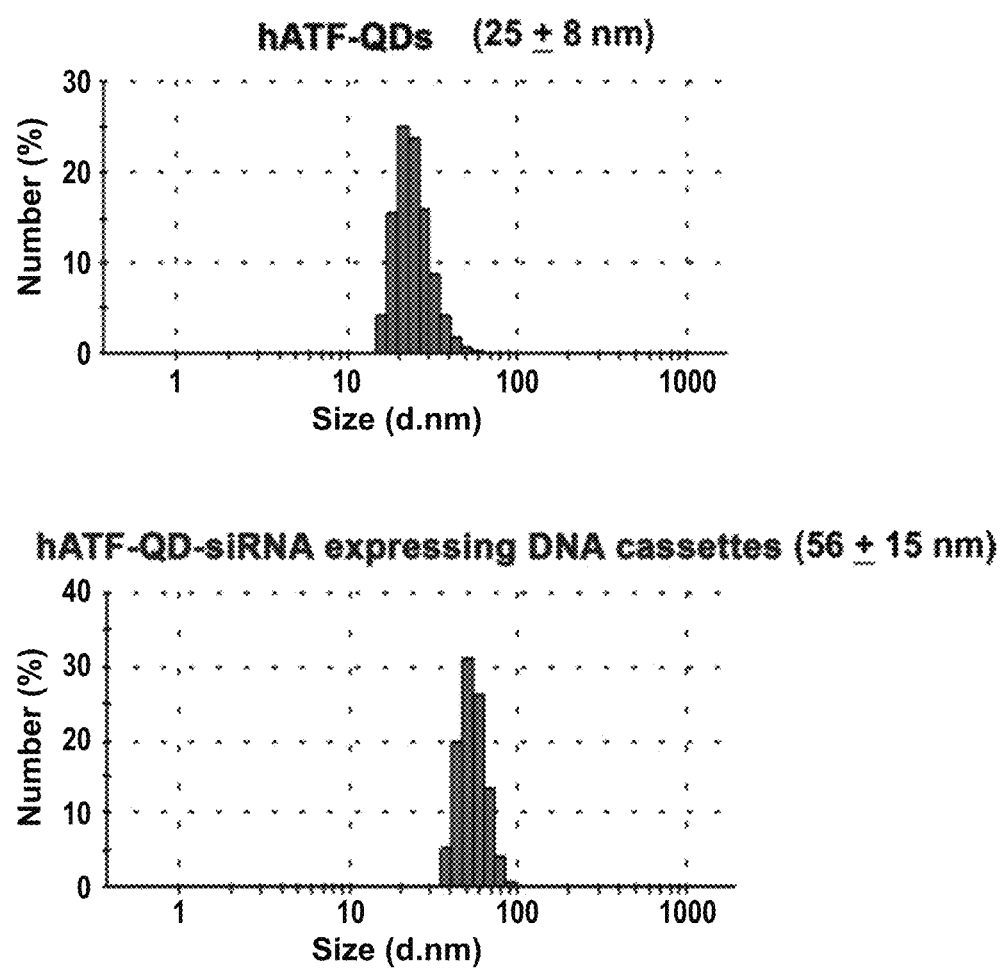

One strategy is to use receptor-targeted nanoparticles for delivering DNA nanocassettes containing the U6 promoter and shRNA gene that are able to express RNA, such as siRNAs, in cells. To enable the production of large amounts of siRNA expressing DNA cassettes by PCR amplification, shRNA expression plasmids were engineered by cloning chemically synthesized double stranded oligonucleotides containing a shRNA gene into a shRNA expression plasmid (p-Silencer 2.1-U6 Neo plasmid) as PCR templates (FIG. 1 A). Two pairs of universal PCR primers were used to amplify 550 or 750 bp double stranded DNA fragments containing the 5'-flank region of the plasmid sequence immediately before the U6 promoter, a U6 promoter, a shRNA gene, and 3'-flank region of the plasmid immediately after the shRNA gene (FIG. 1 A). 550 or 750 bp siRNA expressing DNA nanocassettes were amplified by PCR (FIG. 2 A). These double stranded DNA fragments have molecular weights ranging around 300 to 400 kDa and sizes of several nanometers.

uPAR-targeted nanoparticles carrying siRNA expressing DNA cassettes were then produced by conjugating 17 kDa human ATF (hATF) peptides and DNA nanocassettes to amphiphilic polymer coated QDs or magnetic IONPs (FIG. 1A). Conjugation of hATF and DNA nanocassettes to QDs were determined using gel electrophoresis (FIG. 2B). Conjugation of DNA nanocassettes to QDs did not significantly affect the movement of the QDs in the gel, which may be due to negatively charged DNAs. QDs conjugated with hATF peptides moved much slower compared with QDs alone or QDs-DNA nanocassettes. However, QDs conjugated with both hATF and DNA nanocassettes moved faster than hATF QDs but slower than QDs alone or QDs-DNA-nanocassettes (FIG. 2B). The size distribution of various nanoparticles was examined using a dynamic light scattering measurement. As shown in FIG. 2C, the mean particle size of hATF-QDs is 25±8 nm. Conjugation of ten siRNA DNA nanocassettes increased the particle size to 56±15 nm.

Gene Expression from Double-Stranded DNA Gene-Expressing Nanocassettes

Figure 3A:
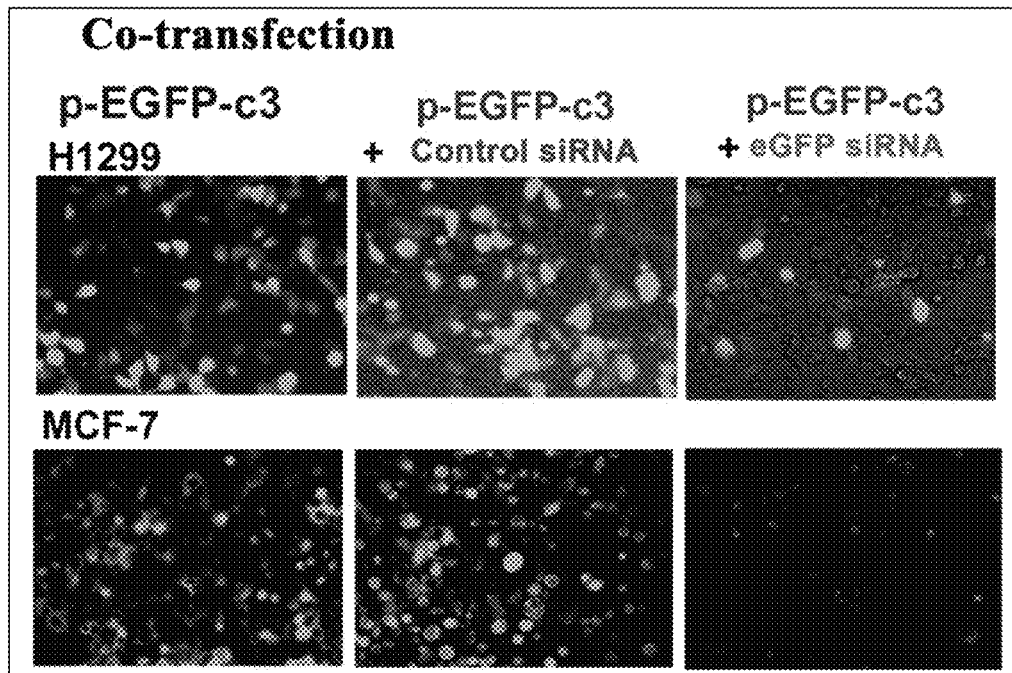
FIG. 3 shows data on gene silencing efficiency using siRNA gene expressing cassettes. A) Determination of siRNA expression from the U6-siRNA DNA cassettes by co-transfection. Upper two panels: H1299 and MCF-7 cancer cells were transfected with p-EGFP-c3, without or with co-transfection with U6-eGFP siRNA or U6-control siRNA expressing nanocassettes for 48 h. B) MCF-7 GFP gene stable cells were transfected with U6-eGFP siRNA or U6-Control siRNA nanocassettes for 48 h.
Figure 3B:
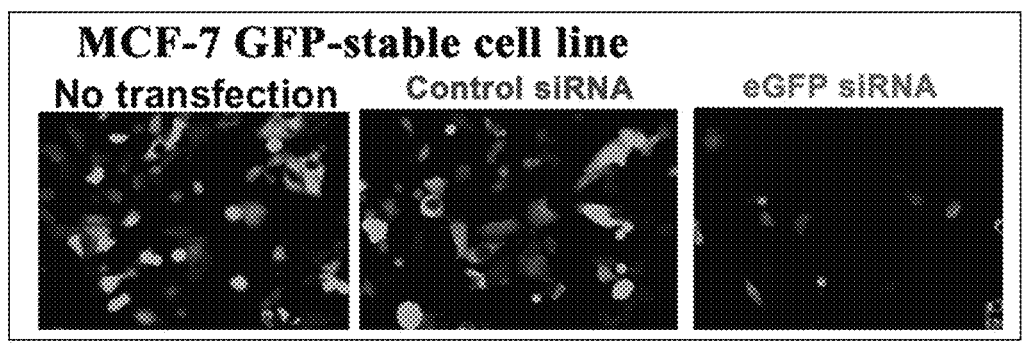

The feasibility and efficiency of gene expression were determined from the DNA-cassettes after being delivered into cells by transfecting cancer cells with 1.8 kb DNA cassettes containing a cytomegalovirus (CMV) promoter and an enhanced green fluorescent protein (EGFP) gene to determine whether the DNA cassettes are capable of producing siRNAs to silence gene expression in cells. U6-eGFP siRNA expressing DNA cassettes were co-transfected with p-EGFP-c3 plasmids into human lung cancer H1299 or breast cancer MCF-7 cells for 48 h. Co-transfection of the U6-eGFP siRNA cassettes markedly inhibited the level of EGFP gene expression in both cell lines (FIG. 3 A). This result was further confirmed by using a GFP gene stable MCF-7 cell line, which showed that transfection of U6-eGFP siRNA nanocassettes silenced the expression of an endogenously transduced EGFP gene (FIG. 3B).

Figure 4A:
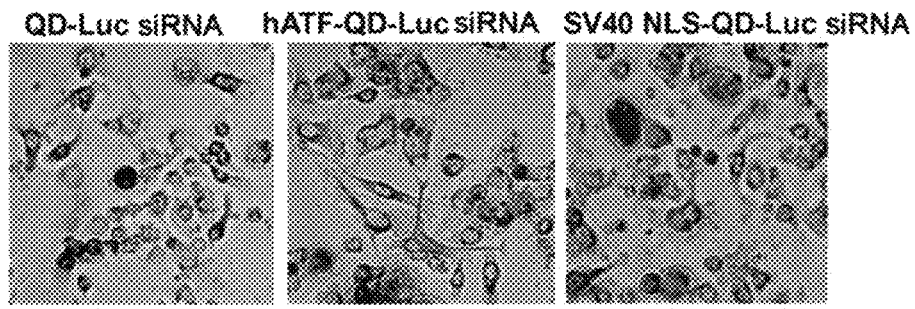
FIG. 4 shows data on uPAR-targeted delivery and gene silencing efficiency of luciferase siRNA-expressing DNA nanocassettes in human tumor cell lines. A) Targeted delivery of Luc siRNA expressing DNA cassettes into human cancer cells. B) Efficiency of gene silencing in cancer cells. Luciferase activity in firefly luciferase gene stably transfected human breast cancer MCF-10DCIS cell lysates was measured at 24 h following nanoparticle incubation. Luciferase units from the no treatment cell lysate serves as 100%. C) Comparison of gene silencing efficiency of delivery of unconjugated RNA-based siRNAs with targeted nanoparticles carrying siRNA expressing DNA nanocassettes. Cells were cultured in 96-well plates and then incubated with 20 pmol of luciferase siRNA (Invitrogen) or an equal molar DNA concentration of ATF-IONP-Luc siRNA expressing cassettes. Luciferase activity in the wells was measured 48 h following the incubation using the Xenogen IVIS system. Luciferase activity of untreated cells serves as 100%.
Figure 4B:
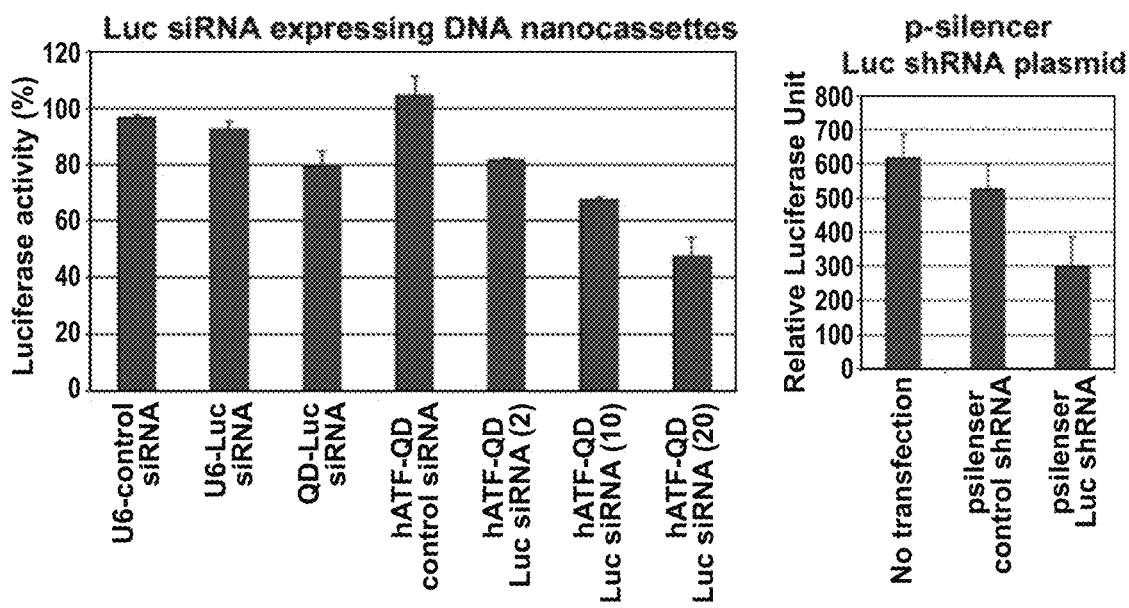

Targeted Delivery of siRNA-Expressing DNA Nanocassettes and Gene-Silencing Efficiency To further quantify gene silencing efficiency in tumor cells in vitro and the detection of dynamic changes in the inhibition of gene expression in animal tumor models in vivo using bioluminescence imaging, U6-luciferase (Luc) siRNA expressing nanocassettes from p-Silencer-firefly luciferase shRNA plasmid were amplified. U6-Luc siRNA nanocassettes were then conjugated to QDs with human ATF targeting ligands. hATF-QDs-Luc siRNA, but not nontargeted QD-Luc siRNA cassettes, could efficiently enter into MCF-10DCIS human breast cancer cells. It has similar intracellular delivery efficiency compared to the SV40-nuclear localization signal (NLS) peptide conjugated-QD-Luc siRNA cassettes (FIG. 4A). uPAR targeted internalization of QD-Luc siRNA led to a decrease in luciferase activity in those cells. The inhibitory effect was enhanced as the copy number of Luc siRNA nanocassettes on each QD increased from 2 to 10 or 20 (FIG. 4B). As a positive control, p-Silencer Luc shRNA plasmids were transfected into the cells and inhibition of luciferase activity was detected in those cells (FIG. 4B).

Figure 4C:
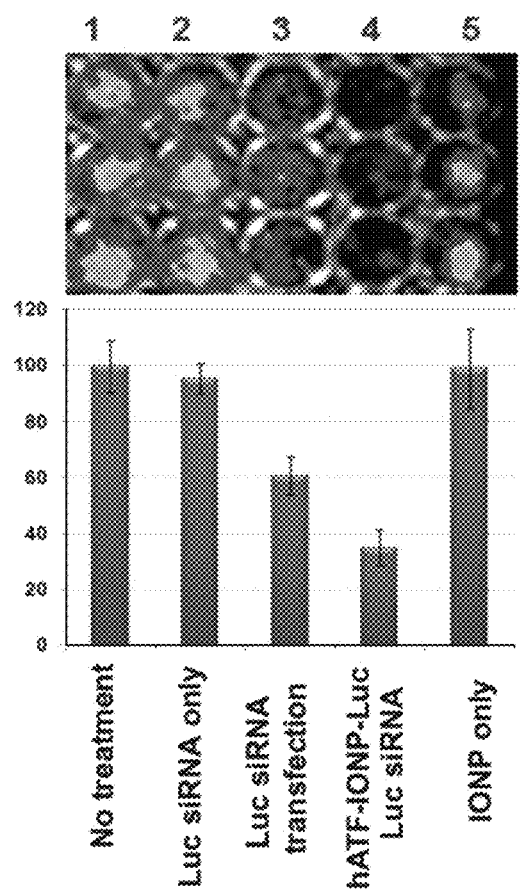

To determine whether targeted delivery of multiple copies of siRNA-generating nanocassettes on a single nanoparticle has a higher efficiency of knocking-down gene expression compared with direct delivery of RNA-based siRNAs, unconjugated double stranded RNA Luc siRNAs or siRNA-expressing DNA cassettes that were conjugated to magnetic IONPs and were delivered into luciferase positive MIA PaCa-2 pancreatic cancer cells. The tumor cells incubated with 20 pmol of DNA equivalent concentration of hATF-Luc siRNA-IONPs for 48 h had 65% reduction in the luciferase activity while transfecting 20 pmol of RNA-based Luc siRNAs decreased the luciferase activity by 39% in the cells (FIG. 4C).

Figure 5A:
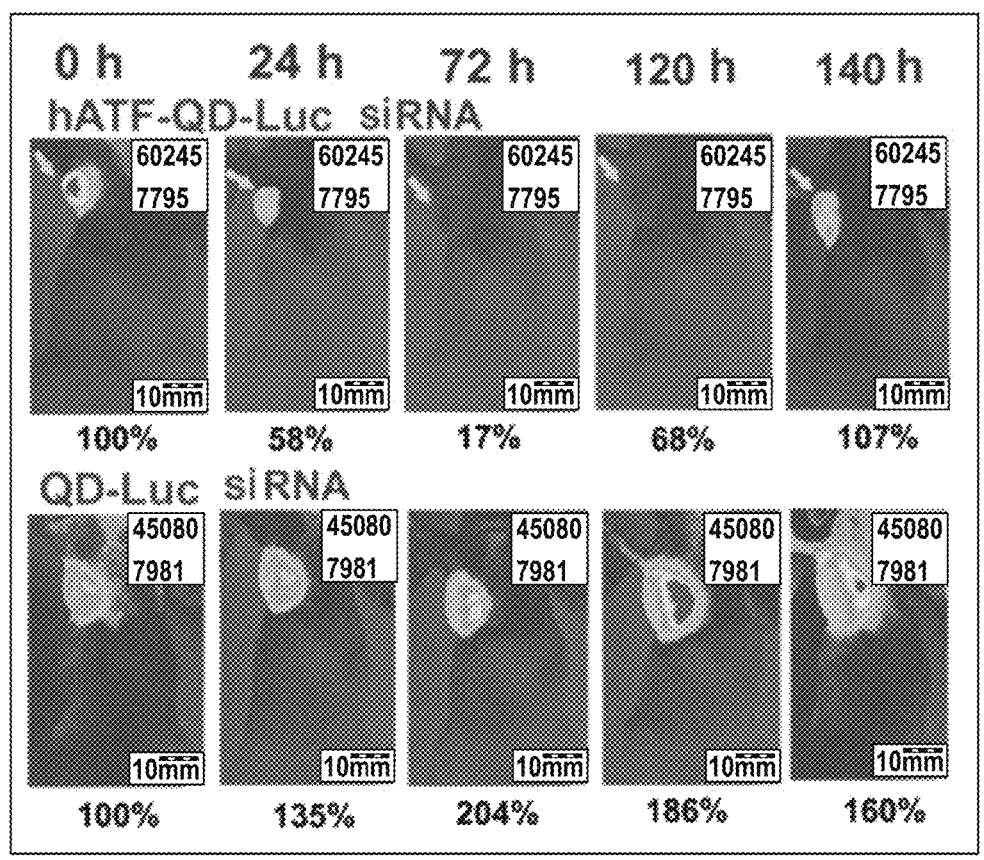
FIG. 5 shows data on targeted delivery of QDs carrying Luc siRNA-expressing DNA nanocassettes silenced the gene expression in human breast cancer xenografts in nude mice. A) Luciferase activity in nude mice bearing MCF-10DCIS human breast tumor xenografts that received hATF-QD-Luc siRNA nanocassettes or non-targeted QD-Luc siRNA nanocassettes. Scale bar: upper right. Same scale was used for all images. Arrows: an orthotopic tumor in the mammary fat pad. B) Examination of biodistribution of QDs carrying siRNA expressing cassettes in frozen tissue sections of tumor and normal organs collected from the mice received a tail vein injection of the nanoparticles for 140 h. Red: QD signal (Em 620 nm). Blue: DAPI nuclear counterstaining. C) Validation of specific gene silencing effect after systemic delivery of hATF-QD-Luc siRNA or control scrambled siRNA-nanocassettes. Bioluminescence images were overlaid with bright-field images of the mice. Numbers in the figure show changes in the percentages of luciferase activity compared with the level in the tumor before the nanoparticle injection. Similar results were observed in three repeat mice in each group.

One of the major obstacles in applying siRNA technology to cancer therapy is the low delivery and gene silencing efficiencies in the tumor following systemic administration. To determine the gene silencing efficiency of uPAR-targeted siRNA expressing nanocassettes, hATF-QD-Luc siRNA nanocassettes were injected via the tail vein into nude mice bearing orthotopic luciferase positive MCF-10DCIS tumors. Non-invasive bioluminescence imaging was used at different time points to determine changes in the luciferase activity in the tumors. Twenty-four hours after the injection, the level of luciferase activity decreased by 42% in the mice that received hATF-QD-Luc siRNA nanocassettes. The inhibitory effect was further enhanced at 72 h and lasted over 120 h after the injection. Although luciferase activity returned to the pre-injection level at 140 h, it is likely that the inhibitory effect was retained in the tumor since the growth of the tumor volume should have significantly increased the luciferase activity, as was shown in the mouse found with 160% increase in luciferase activity at 140 h after receiving non-targeted QD-Luc siRNA nanocassettes (FIG. 5A). The mouse that received non-targeted QD-Luc siRNA nanocassettes showed increases in luciferase activity at time points following system delivery (FIG. 5A).

Figure 5B:
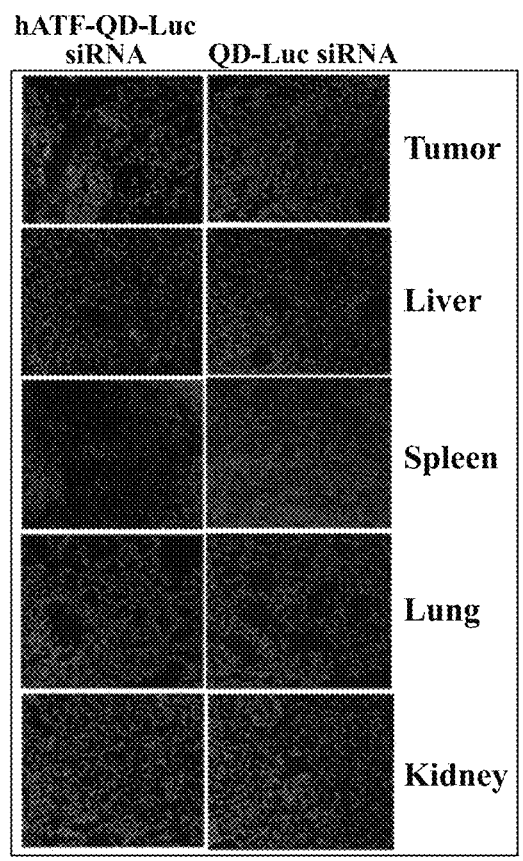

Selective delivery of the targeted nanoparticles into the tumors was further confirmed by histological analysis of the tumor and normal tissues collected from the mice following systemic delivery of 200 pmol of the targeted or non-targeted QDs (FIG. 5B) and by ex vivo optical imaging of tumor and normal organs. In the mice that received uPAR-targeted QDs-carrying Luc siRNA nanocassettes, strong red QD signals were found in the tumors (FIG. 5B). However, QD signal was not found in the mice that received non-targeted QD-Luc siRNAs (FIG. 5B). Furthermore, the levels of QD accumulation in the liver and spleen of the mice that received the targeted QD-Luc siRNA cassettes were markedly decreased compared with those of the mice injected with non-targeted QDs (FIG. 5B). QD signal was not detected in the lung, kidney and heart in the mice that received either targeted or non-targeted nanoparticles (FIG. 5B).

Figure 5C:
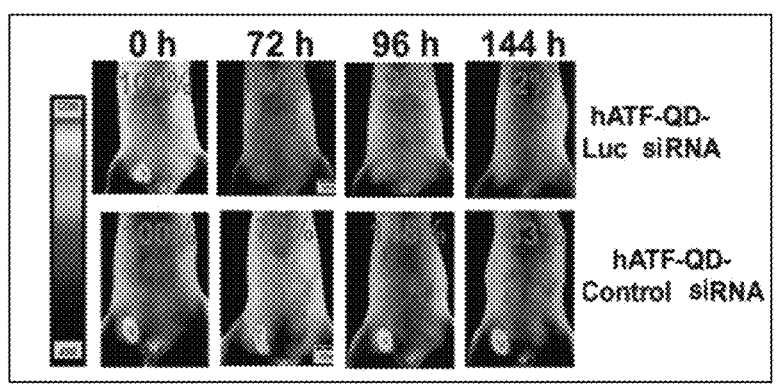

To determine whether the changes in luciferase activity in the tumor were the result of specific silencing of the luciferase gene, mice bearing MCF-10DCIS tumors in the low abdominal mammary gland received a tail vein injection of either hATF-QD-Luc siRNA or hATF-QD-control siRNA nanocassettes. Consistent with the above observation, a significant decrease in luciferase activity (>90%) was detected in the tumor at 72 h and the inhibitory effect was still strong at 144 h following the injection (FIG. 5C). However, only a moderate decrease in luciferase activity (17 to 28%) was detected in the tumors of mice receiving hATF-QD control siRNA nanocassettes (FIG. 5C). Therefore, the effect of down regulation of luciferase gene expression is likely due to the targeted delivery of luciferase siRNA-expressing nanocassettes into the tumor.

Figure 6A:
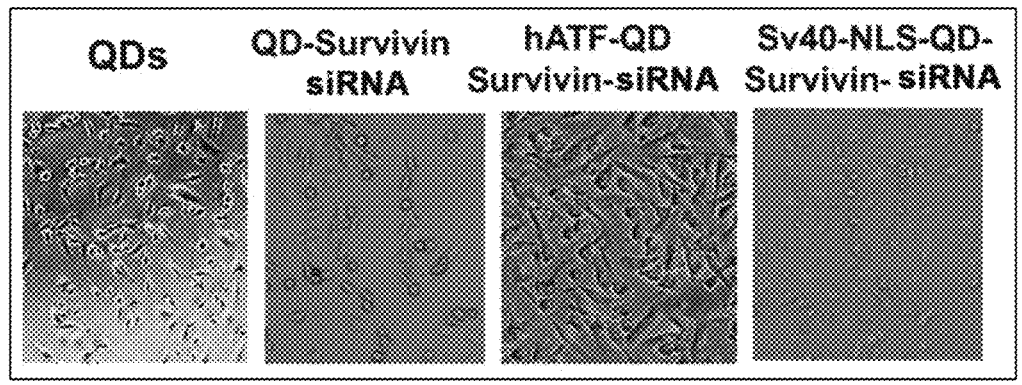
FIG. 6 shows data on targeted silencing of survivin gene expression in human tumor cells A) Internalization of hATF-QD-Survivin siRNA expressing DNA cassettes by MDA-MB-231 breast cancer cells. B) Western blot analysis. Following treatment, cell lysates were then collected for Western blot analysis using antibodies against survivin or caspase 3. Activation of caspase 3 is shown as the detection of the cleaved caspase 3 fragments (low molecular weight bands at 17 kDa). C) Effect of nanoparticle delivery of Survivin-siRNA nanocassettes. Left panel: Fluorescent images show internalization of hATF-QD-Survivin siRNA nanocassettes in MIA PaCa-2 pancreatic cancer cells. Red: QD signal. Right panel: Crystal violet cell proliferation assay 2 days following treatment. O.D. value of no treatment group was used as 100%.
Figure 6B:
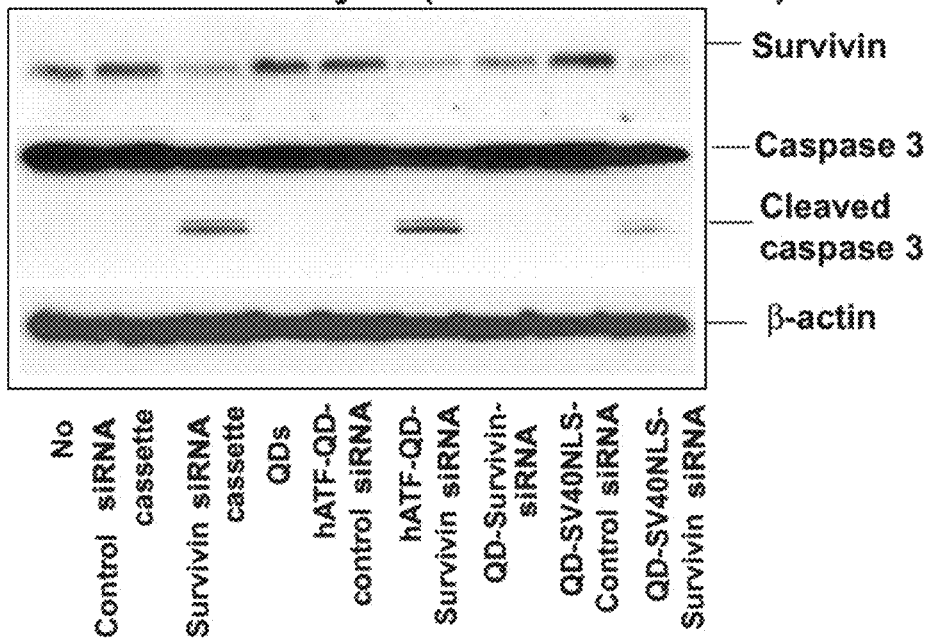
Figure 6C:
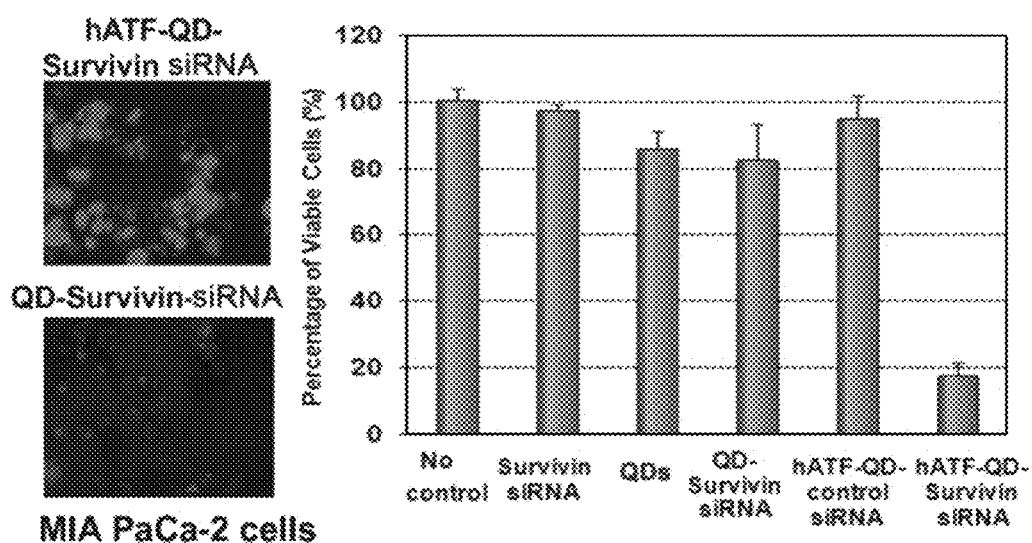

Targeted Delivery of Survivin siRNA Nanocassettes Using Nanoparticles on Cell Death Induction and Drug Sensitivity in Human Cancer Cells Taking advantages of the specific gene knock-down function of siRNA-expressing DNA nanocassettes, uPAR-targeted QDs carrying survivin siRNA expressing nanocassettes were produced and a high efficiency of intracellular nanoparticle delivery in MD-MB-231 breast cancer cells was found (FIG. 6A). Survivin is an anti-cell death gene that confers resistance of cancer cells to therapeutic agents. Western blot analysis revealed that the level of survivin proteins was markedly down-regulated in cells transfected with surviving siRNA expressing nanocassettes (FIG. 6B). In cultured cells, the targeted gene knock-down effect by hATF-QD survivin siRNA expressing DNA nanocassettes was similar as that of SV40-NLS-mediated internalization of the QD surviving siRNA nanocassettes (FIG. 6B). However, SV40-NLS-QD-siRNA nanocassettes could not be used for in vivo delivery due to the lack of specificity. Inhibition of survivin expression led to the activation of the apoptotic cell death since a high level of active caspase 3 (17 KDa fragments) was detected in those cell groups by Western blot analysis (FIG. 6B). Targeted internalization of hATF QD-survivin siRNA expressing nanocassettes were further confirmed in the MIA PaCa-2 cell line (FIG. 6C). Treatment of the pancreatic cancer cells with hATF-QD-Survivin siRNA expressing nanocassettes for 2 days induced cell death and significantly reduced the percentage of viable cells (FIG. 6C). However, there was no significant change in the percentage of viable cells that received QDs only, non-targeted QD-survivin siRNA nanocassettes, or hATF-QD-Control siRNA nanocassettes (FIG. 6C).

Figure 7A:
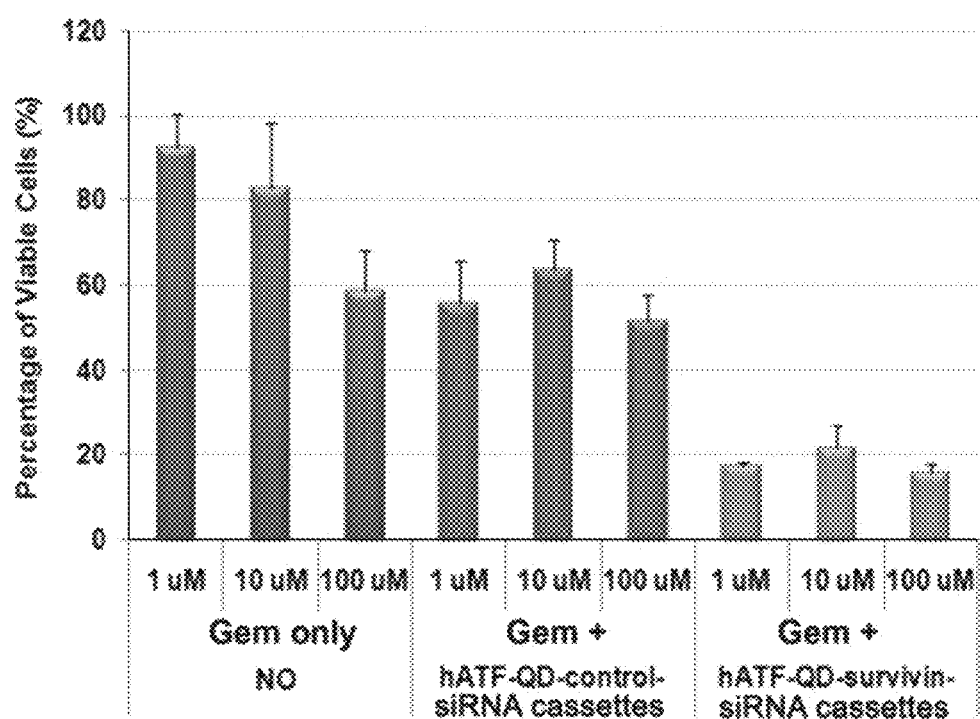
FIG. 7 shows data on the combination effect of survivin gene silencing and drug treatment A) Cell proliferation assay. The O.D. value of no treatment cells was used as 100%. Student's t-test: Gem only vs. Gem+hATF-QD-Survivin siRNA expressing cassettes, $p<0.0005$ for all three concentrations. B) Caspase 3 activity assay. O.D. value from the non-treated cell lysate was used as 1.
Figure 7B:
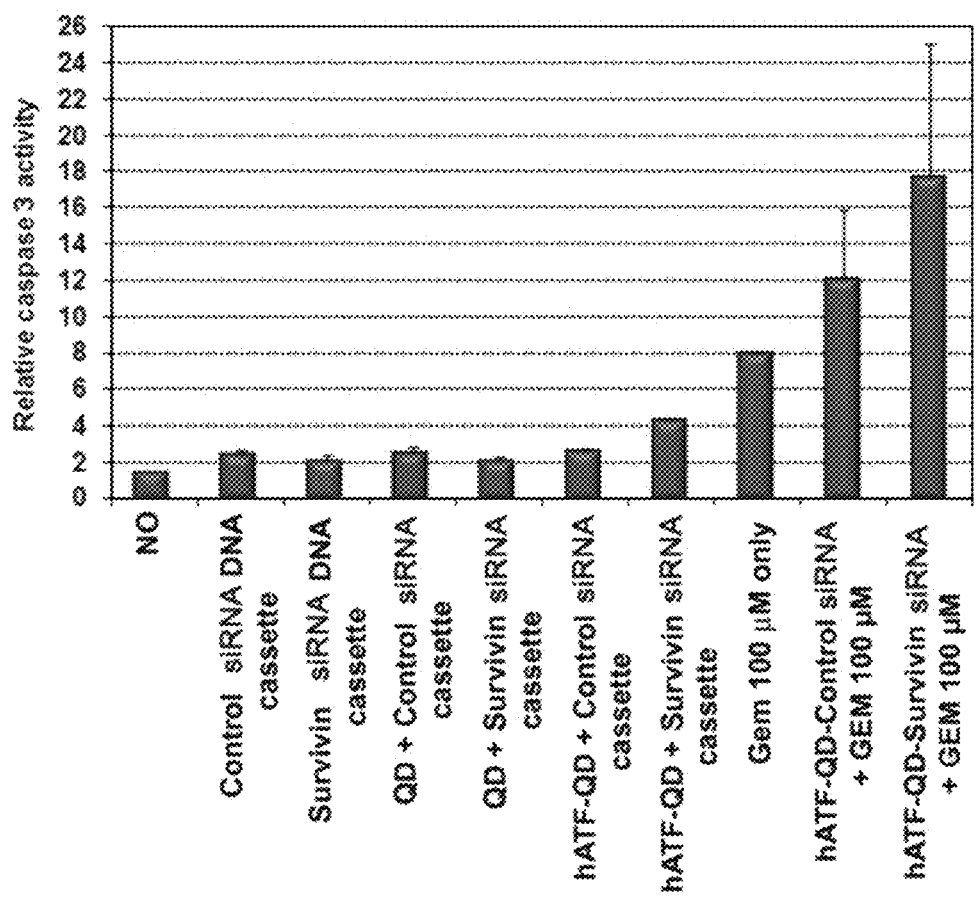

The effect of survivin gene silencing using hATF-QD-Survivin siRNA expressing nanocassettes was examined on cell sensitivity to chemotherapy drugs. MIA PaCa-2 cancer cells were treated concomitantly with a chemotherapy drug, gemcitabine, and hATF-QD-Survivin siRNA or hATF-QD-Control siRNA expressing nanocassettes. Pancreatic cancer cells have a low sensitivity to free gemcitabine treatment and 60% of viable cells were detected by cell proliferation assay 72 h following 100 µM of gemcitabine treatment (FIG. 7A). However, co-treatment of gemcitabine with hATF-QD-Survivin siRNA expressing nanocassettes significantly enhanced the inhibitory effect on tumor cell growth at all drug concentrations (p<0.0005, student's-t test). For example, the combination of knocking-down survivin gene with 1 µM of gemcitabine treatment significantly decreased the percentage of viable cells from 94% in free drug treated group to 18% in cells that received combination therapy (FIG. 7A). We further demonstrated that the enhanced effect on tumor cell growth inhibition is due to the activation of the apoptotic cell death pathway since a high caspase 3 activity was detected in cells treated with the combination of gemcitabine with hATF-QD-Survivin siRNA expressing nanocassettes (FIG. 7B).

Human Cancer Cell Lines

H1299 human lung, MCF-7 and MDAMB-231 human breast, and MIA PaCa-2 human pancreatic cancer cell lines were obtained from the American Type Culture Collection (ATCC, Manassas, Va.) and cultured in the medium as suggested by the ATCC. The MCF-10DCIS (or MCF-10DCIS.com) human breast cancer cell line was obtained from Dr. Fred Miller at the Barbara Ann Karmanos Cancer Institute (Detroit, Mich.) and cultured in the DMEM/F12 medium supplemented with 5% horse serum. The dual firefly luciferase and enhanced green fluorescence protein (eGFP) gene stable MCF-10DCIS cell line was produced by transducing cells with a lentiviral vector, LV-pUB-Fluc-eGFP. Firefly luciferase gene stable MIA PaCa-2 human pancreatic cancer cell line was kindly provided by Dr. Rosa Hwang, MD Anderson Cancer Center, Houston, Tex.

Engineering siRNA Expressing Plasmids

The shRNA expressing plasmids were generated by cloning 69 to 77 nt of chemically synthesized double stranded oligonucleotides (Sigma Aldrich, St. Louis, Mo.) containing the following structure: 5'-GGATCC(Bam H1)-$X_n$(nt shRNA sense sequences)-TTCAAGAGA (Loop sequence)-$Y_m$ (shRNA antisense sequences)-TTTTTTGGAAA (Terminate sequence)-AAGCT (Hind III) (SEQ ID NO: 1), wherein X and Y are nucleotides, n is about 19 to 23, m is about 19 to 20, into Bam H1-Hind III cloning site of p-Silencer 2.1-U6 Neo plasmid (Ambion/Invitrogen, Grand Island, N.Y.). The following are siRNA sense sequences used included: 1) Random control: 5'-AAGAGGCTTGCAACA-GTGCA-3' (SEQ ID NO: 2); 2) Survivin: 5'-GAGGCTG-GCTTCATCCACTGCCC-3' (SEQ ID NO: 3); 3) Firefly luciferase:

5'-CGGATTACCAGGGATTTCA-3' (SEQ ID NO: 4); and 4) Enhanced green fluorescence protein (EGFP) 5'-CAAGCTGACCCTGAAGTTC-3' (SEQ ID NO: 5). After demonstrating their effects on the down regulation of gene expression in tumor cell lines following transfection, these p-Silencer shRNA plasmids were used as templates for PCR amplification of the DNA cassettes (FIG. 1A).

For HIF-1 alpha an exemplary sense strand is 5'-CAGTG-GATTACCACAGCTGA-3' (SEQ ID NO: 11) in SEQ ID NO: 1.

PCR Amplification of siRNA-Expressing DNA Cassettes

Two pairs of universal PCR primers were used to amplify the double stranded DNA cassettes from the p-Silencer shRNA plasmids. The PCR primer pair for the small cassette was: 5'-GATGTGCTGCAAGGCGATTA-3' (SEQ ID NO: 6) (Forward) and 5'-AGTGAGCGCAACGCAATT-3' (SEQ ID NO: 7) (Reverse). The primer pair for the large cassette was: 5'-AACTGTTGGGAAGGGCGA-3' (SEQ ID NO: 8) (Forward) and 5'-AGTGAGCGCAACGCAATT-3' (SEQ ID NO: 9) (Reverse). Both reverse primers were modified at the 5' end with an amine group for conjugation to a nanoparticle. To protect the DNA cassettes from digestion by deoxyribonucleases, the reverse primers were also modified at the 5' end with a phosphorothioate linkage (FIG. 1 A). Using p-Silencer shRNA plasmids as templates and above PCR primer pairs, 550 bp or 750 bp of firefly luciferase, survivin, GFP, and control siRNA expressing DNA cassettes were amplified using the following PCR conditions: 95° C. for 5 min; 94° C. for 30 s, 55° C. for 30 s, 72° C. for 90 s, 30 cycles; and 72° C., 8 min. PCR samples were then ethanol precipitated and re-suspended in $H_2O$. DNA fragments were purified from the gel using the QIAEX II Agarose Gel Extraction Kit (Qiagen, Valencia, Calif.).

Production of uPAR-Targeted Nanoparticles Carrying siRNA Expressing DNA Nanocassettes The recombinant amino terminal fragment (ATF, 135 aa) of human uPA (17 kDa) was produced from *E. coli* BL21 bacterial expression system using a pET20a plasmid (Invitrogen, Grand Island, N.Y.) containing the ATF cDNA sequence. Recombinant human ATF (hATF) was purified from bacterial extracts using a Ni2+ NTA-agarose column (Qiagen). uPAR-targeted nanoparticles carrying siRNA expressing DNA cassettes were produced by two steps. First, hATF peptides were conjugated to amphiphilic polymer coated quantum dots (QDs, emission wavelength 620 nm, Ocean Nanotech, LLC, Springdale, Ark.) or magnetic iron oxide nanoparticles (IONPs, 10 nm core size, Ocean Nanotech, LLC) at a molar ratio of 1 nanoparticle to 10 hATF by forming an amide bond between the amine group of hATF and the carboxyl group of the amphiphilic polymer, mediated by 1-ethyl-3-(3-dimethylaminopropyl)carbodiimide (EDAC) and sulfo-NHS (Pierce, Rockford, Ill.). Nanoconjugates were purified using the Nanosep 100 k column (Pall Corp, Ann Arbor, Mich.). Purified PCR fragments were then conjugated to hATF-nanoparticles at a ratio of 1 nanoparticle:10 or 20 DNA cassettes by EDAC mediated conjugation of the 3'-terminal amine group of the DNA fragments with the carboxyl group of the polymer coating (FIG. 1A). Conjugated nanoparticles were purified using a magnet sorter (Ocean Nanotech, LLC) at 4° C. overnight. After conjugation, the nanoparticles were diluted and examined for particle size distribution using a Zetasizer Nano (Malvern Instruments Inc., Southborough, Mass.). Conjugation of DNA cassettes and ATF peptides to QDs was examined by electrophoresis in 0.8% agarose gel for 1 h. The gel was stained with SYBR green DNA dye, and examined by the Olympus OV-100 imaging system (Olympus America Inc., Central Valley, Pa.).

Cell Transfection

Cells were co-transfected with pEGFP-c3 plasmids and U6-eGFP siRNA or U6-control siRNA expressing DNA nanocassettes using Lipofectamine 2000 Reagent (Invitrogen). MCF-7 GFP gene stable cells, kindly provided by Dr. Adam Marcus at Emory University, were transfected with U6-eGFP siRNA or U6-Control siRNA expressing cassettes for 48 h and then examined under an inverted fluorescence microscope. 3 μg of DNA or DNA equivalent amount of QDs were used for above studies.

Determination of Target Specificity of hATF-Conjugated Nanoparticles

Cells were plated in 24-well culture plates for 24 h and then incubated with various nanoparticles at an equal molar concentration (15 pmol of QDs) for 24 h. Control unconjugated DNA cassettes or plasmids were transfected into cells. As a delivery efficiency control, siRNA expressing nanocassettes were also conjugated to QDs with the NLS peptides from SV40 virus, CGGGPKKKRKVE (SEQ ID NO: 10). The peptide sequence was provided by Dr. Steven Dowdy at University of California, San Diego. The SV-40-NLS peptides were synthesized by Genscript USA Inc. (Piscataway, N.J.). Culture plates were then examined using an inverted Olympus fluorescence microscope.

Luciferase Activity Assay

Following different treatments, cells were collected from culture plates. Cell lysates were examined for luciferase activity using the Single Luciferase Assay System (Promega Corp., Madison, Wis.). The level of the luciferase activity was measured by a luminometer (Lumistar galaxy, BMG, Winooski, VM) for single samples or using the Xenogen IVIS system (Caliper Life Sciences, Mountain View, Calif.) for 96-well plates.

Western Blot Analysis

Cells were incubated with various QDhATF/survivin-siRNA expressing DNA nanocassettes or non-targeted QD-survivin siRNA expressing DNA nanocassettes for 48 h.

Control siRNA and survivin siRNA DNA nanocassettes were transfected into MDA-MB-231 cells. After treatment, cells were lysed with cell lysis buffer. A total of 30-50 μg of the proteins were resolved on 12% polyacrylamide-SDS gels and then transferred to PVDF membranes (Bio-Rad laboratories, Hercules, Calif.). The membranes were blocked with 5% nonfat milk in Tris-buffered saline for 1 h, and incubated overnight with primary antibodies for survivin, caspase-3, and β-actin (Santa Cruz Biotechnology, Santa Cruz, Calif.). After three washes, the membranes were incubated with anti-goat, anti-rabbit, or anti-mouse secondary antibodies conjugated with horseradish-peroxidase (Santa Cruz Biotechnology) for 1 h. The levels of specific proteins in each lysate were detected by enhanced chemiluminescence using ECL plus (Amersham International, Buckingham, UK) followed by autoradiography.

Cell Proliferation Assay

Crystal violet assay was used to determine the percentage of viable cells. Cells were plated in 96-well culture plates for 24 h and then treated with various nanoparticles or transfected with survivin siRNA expressing DNA cassettes for 48 h. To detect drug sensitivity, MIA PaCa-2 cells were treated with gemcitabine (Eli Lilly Co., Indianapolis, Ind., USA) without or with nanoparticles carrying survivin siRNA expressing DNA cassettes for 48 h. Cells were fixed with 4% paraformaldehyde in PBS and then stained with crystal violet. Percentage of viable cells in the experimental groups was determined by measurements O.D. at 590 nm using Spectra Max Plus (Molecular Devices, Sunnyvale, Calif.). Caspase 3 Activity Assay:MIA PaCa-2 cells were treated with various nanoparticles in the presence or absence of gemcitabine for 48 h. Cell lysates were analyzed for their levels of caspase 3-like activity, which is generated by caspases 3, 7, and 10, using an Ac-DEVD-AFC substrate (Calbiochem, San Diego, Calif.). Measurements were made using a fluorescence microplate reader (Spectra Max Gemini xs, Molecular Devices) at an excitation wavelength of 408 nm and an emission wavelength of 500 nm.

Detection of Targeted Delivery and Gene Silencing Effects in an Animal Tumor Model An orthotopic human breast cancer xenograft model was established by injecting $1 \times 10^7$ of dual firefly luciferase and GFP positive MCF-10DCIS cells into the mammary fat pad of the nude mice. The tumor bearing mice then received 200 pmol of QDs carrying luciferase siRNA-expressing DNA cassettes (about 2 nmol of DNA cassettes) by tail vein injection. Before and at different time points following the nanoparticle administration, 2 mg/Kg of luciferin substrate was injected intraperitoneally into the mice for 5 min before each bioluminescence imaging procedure using identical imaging conditions and an Olympus OV-100 small animal imaging system (Olympus America Inc.).

The invention claimed is:

1. A nanoparticle comprising a core comprising iron oxide with polymer coating wherein the polymer coating is conjugated to a double stranded deoxyribonucleic acid having between about 350 and 750 base pairs that encodes a RNA capable of RNA interference in operable combination with a promoter and wherein a cell targeting molecule is amino terminal fragment (ATF) of the urokinase plasminogen activator (uPA) and is conjugated to the polymer coating, wherein a covalent bond is between the nanoparticle and the deoxyribonucleic acid, wherein the nanoparticle has a size of less than 100 nm, and wherein the RNA capable of RNA interference is RNA that forms a hairpin.

2. The nanoparticle of claim 1, wherein the RNA capable of RNA interference comprises a survivin sequence of greater than 15 nucleotides.

3. The nanoparticle of claim 1, wherein the promoter is U6 or H1.

4. The nanoparticle of claim 1 further comprising an anticancer agent.

* * * * *